US 6,524,318 B1

(12) United States Patent
Longhini et al.

(10) Patent No.: US 6,524,318 B1
(45) Date of Patent: Feb. 25, 2003

(54) SPINAL SURGERY INSTRUMENTS AND METHODS

(75) Inventors: Ross Longhini, Woodbury, MN (US); John J. Grabowski, Bloomington, MN (US); Kevin V. Guenther, Carver, MN (US); Erik E. Emstad, St. Paul, MN (US); Peter J. Pohndorf, Stillwater, MN (US)

(73) Assignee: Sulzer Spine-Tech Inc., Minneapolis, MN (US)

( * ) Notice: Subject to any disclaimer, the term of this patent is extended or adjusted under 35 U.S.C. 154(b) by 0 days.

(21) Appl. No.: 09/484,045

(22) Filed: Jan. 18, 2000

Related U.S. Application Data

(63) Continuation-in-part of application No. 09/420,070, filed on Oct. 18, 1999, now abandoned.

(51) Int. Cl.[7] ................................................. A61F 5/00
(52) U.S. Cl. ........................................................ 606/86
(58) Field of Search ........................... 606/86, 96, 99, 606/104, 108, 61, 53

(56) References Cited

U.S. PATENT DOCUMENTS

| | | | |
|---|---|---|---|
| 3,857,389 A | * 12/1974 | Amstutz | 128/92 EC |
| 3,875,595 A | 4/1975 | Froning | |
| 4,545,374 A | 10/1985 | Jacobson | |
| 4,573,448 A | 3/1986 | Kambin | |
| 4,616,638 A | * 10/1986 | Griggs | 128/92 BB |
| 4,686,972 A | 8/1987 | Kurland | |
| 4,714,469 A | * 12/1987 | Kenna | 623/17 |
| 4,877,020 A | 10/1989 | Vich | |
| 4,878,915 A | 11/1989 | Brantigan | |
| 4,961,740 A | 10/1990 | Ray et al. | |
| 5,015,247 A | 5/1991 | Michelson | |
| 5,026,373 A | 6/1991 | Ray et al. | |
| 5,055,104 A | 10/1991 | Ray | |
| 5,306,278 A | * 4/1994 | Dahl et al. | 606/96 |
| 5,458,638 A | 10/1995 | Kuslich et al. | |
| 5,484,437 A | 1/1996 | Michelson | |
| 5,489,307 A | 2/1996 | Kuslich et al. | |
| 5,489,308 A | 2/1996 | Kuslich et al. | |
| 5,505,732 A | 4/1996 | Michelson | |
| 4,961,740 A | 1/1997 | Ray et al. | |
| 5,609,636 A | 3/1997 | Kohrs et al. | |
| 5,658,337 A | 8/1997 | Kohrs et al. | |
| 5,722,977 A | * 3/1998 | Wilhelmy | 606/84 |
| 5,741,253 A | 4/1998 | Michelson | |
| 5,772,661 A | 6/1998 | Michelson | |
| D397,436 S | 8/1998 | Michelson | |
| 5,797,909 A | 8/1998 | Michelson | |
| 6,042,582 A | 3/2000 | Ray | |
| 6,113,602 A | 9/2000 | Sand | |
| 6,113,638 A | * 9/2000 | Williams et al. | 623/17 |
| 6,224,599 B1 | 5/2001 | Baynham et al. | |

FOREIGN PATENT DOCUMENTS

| EP | 0 796 593 A2 | 9/1997 |
|---|---|---|
| WO | WO 00/59413 | 10/2000 |

OTHER PUBLICATIONS

"Anterior 4021 Tooth Tube Surgical Technique, BAK™ Interbody Fusion System," *Sulzer Spine–Tech*, undated.

(List continued on next page.)

Primary Examiner—Eduardo C. Robert
(74) Attorney, Agent, or Firm—Merchant & Gould P.C.

(57) ABSTRACT

Instruments and methods for insertion of one or more spinal implants into an intervertebral space between opposing vertebral bodies are disclosed. Instruments according to the invention include a guide for preparing a spinal fusion implant site, a guide starter, implant depth gauges, reamers, taps and implant drivers. The instruments and methods disclosed provide improved visualization of the surgical field and enhanced precision of placement of spinal fusion implants between vertebral bodies.

16 Claims, 18 Drawing Sheets

OTHER PUBLICATIONS

"Posterior 4022 Paddle Tube Surgical Technique, BAK™ Lumbar Interbody Fusion System," *Sulzer Spine–Tech*, undated.

"Posterior 4022 Tooth Tube Surgical Technique, BAK™ Limbar Interbody Fusion System," *Sulzer Spine–Tech*, undated.

"Surgical Technique Using Bone Dowel Instrument," *Sofamor Danek, The Spine Specialist*, undated.

* cited by examiner

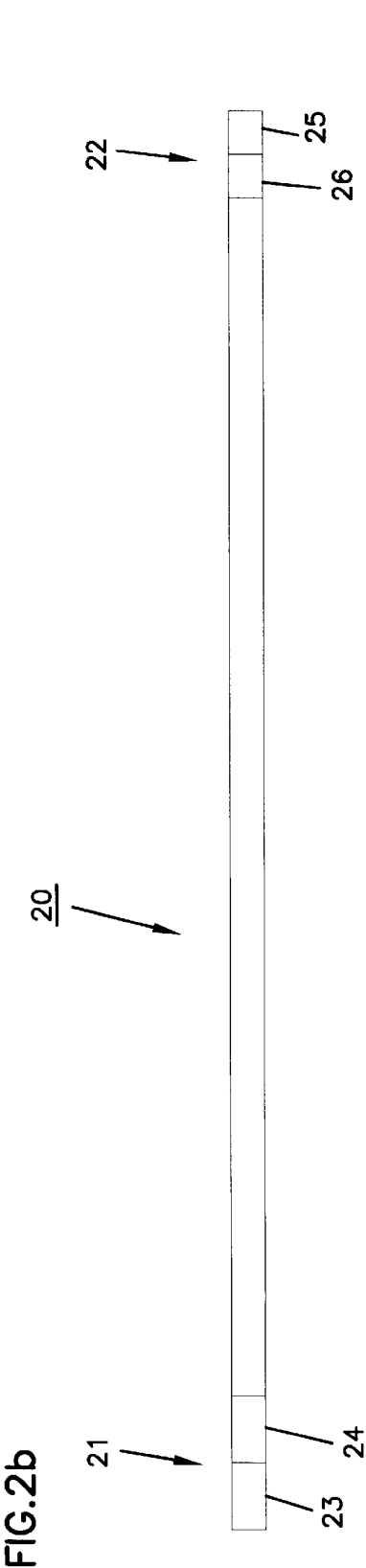
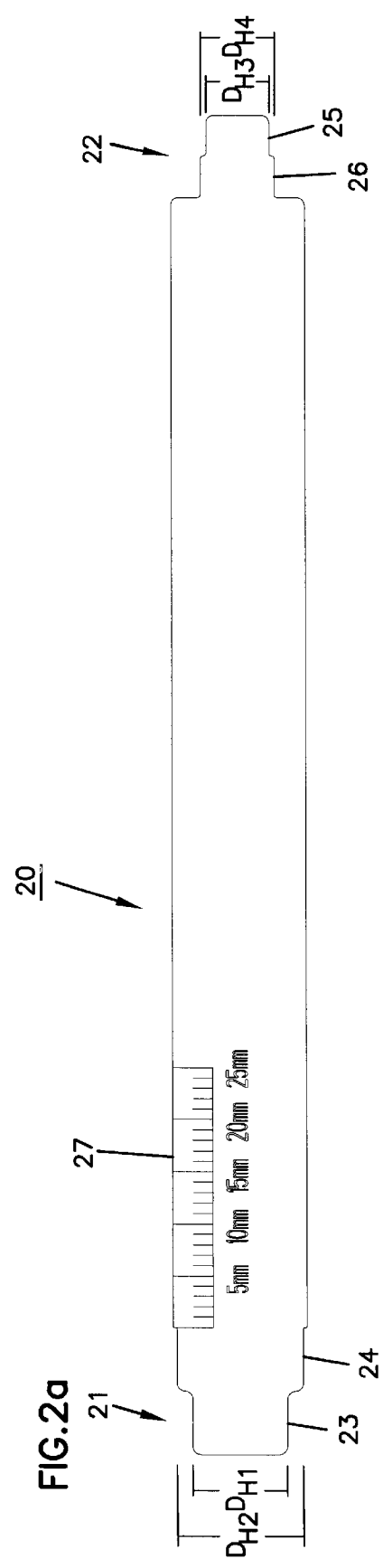

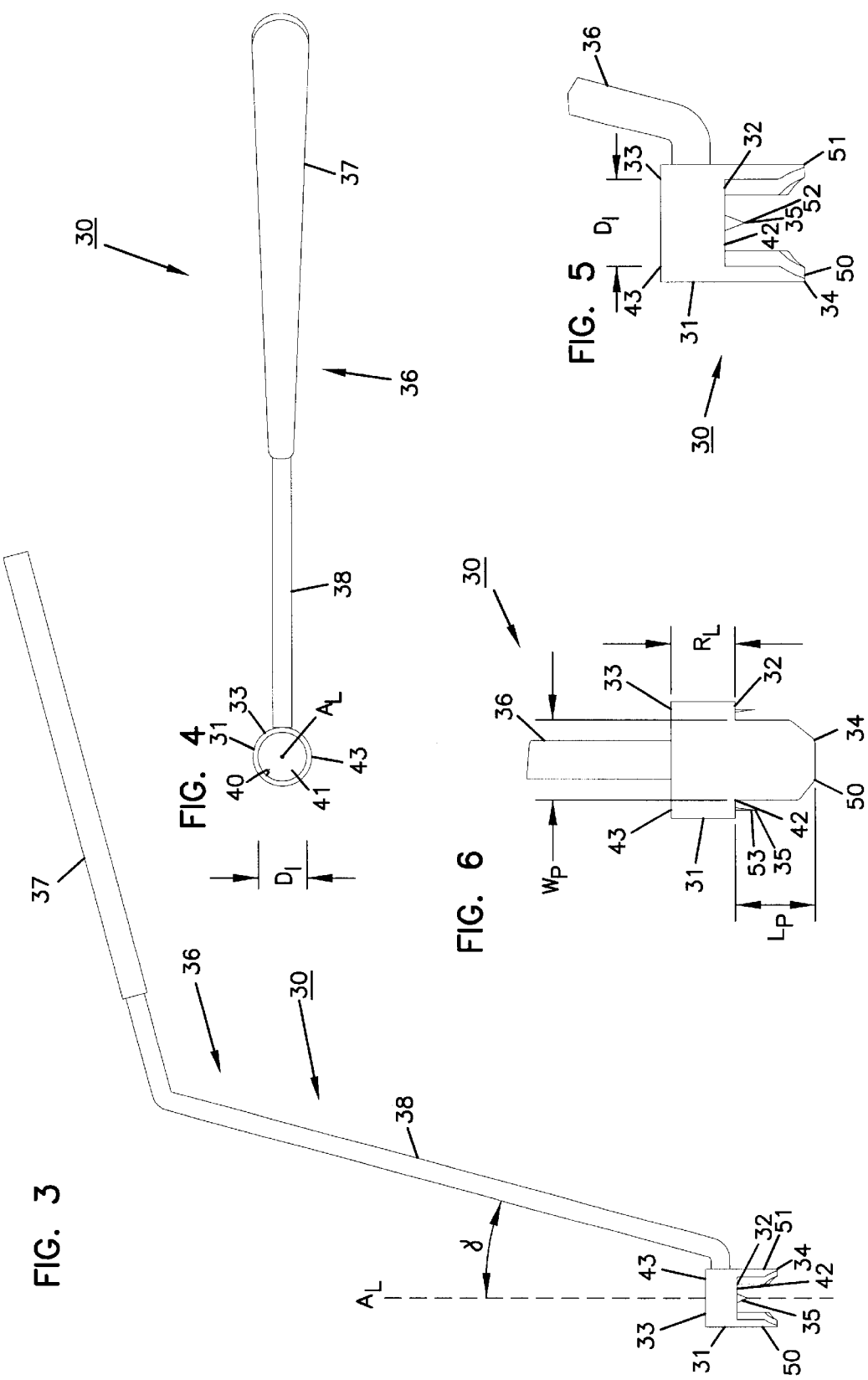

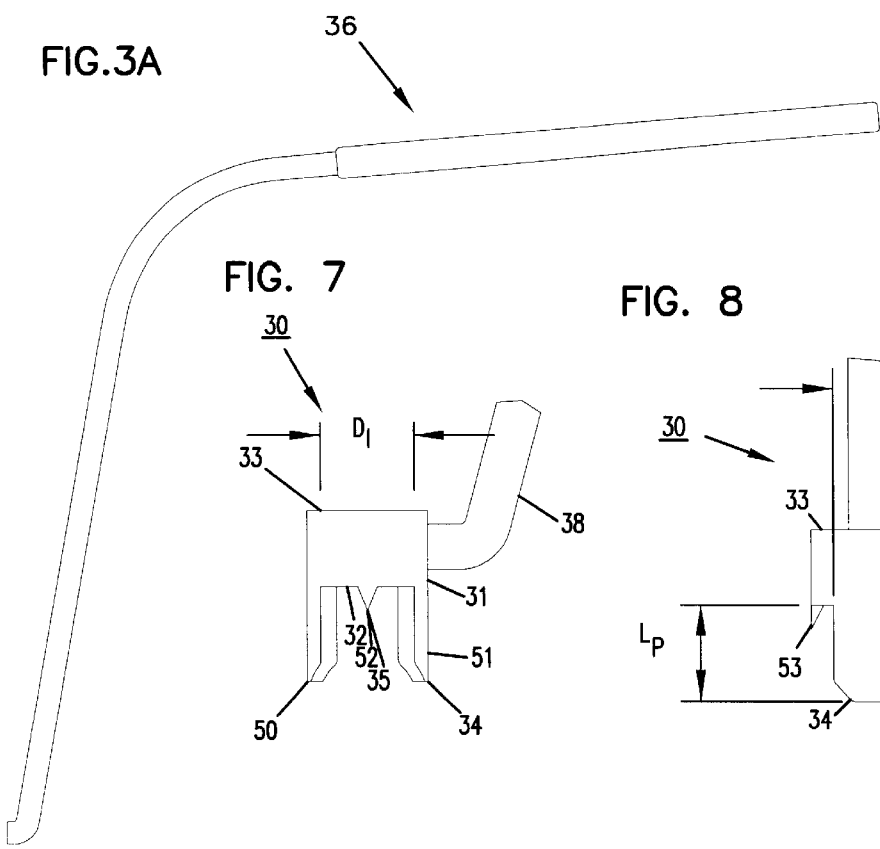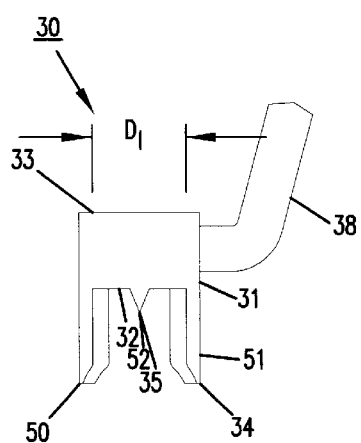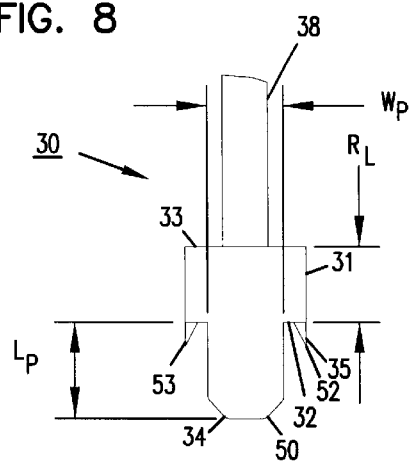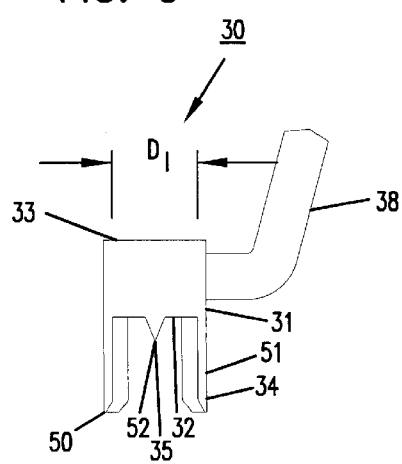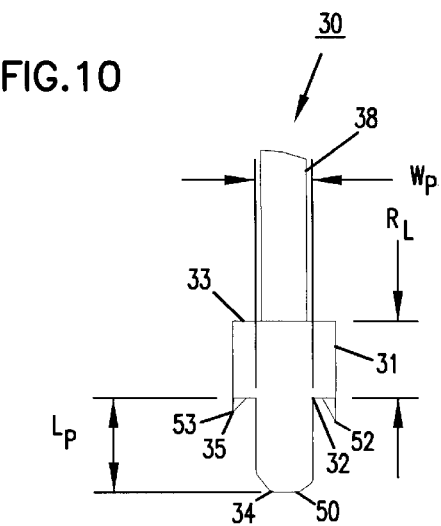

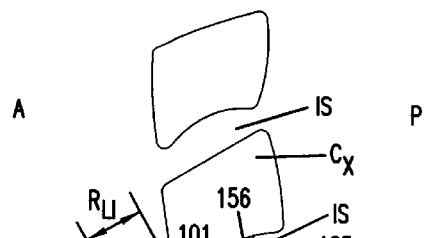
FIG.12
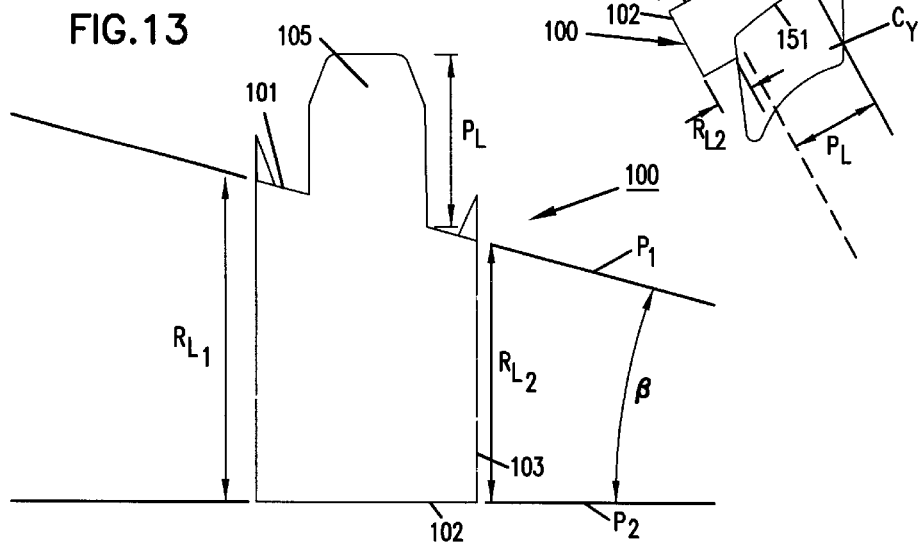
FIG.13
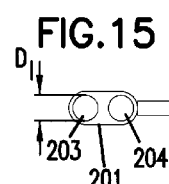
FIG.14
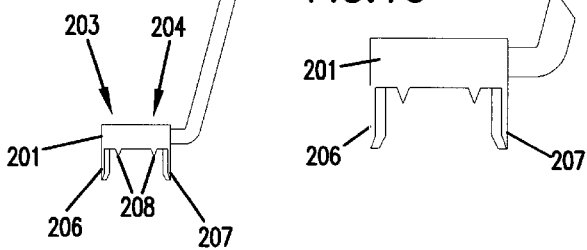
FIG.15
FIG.16
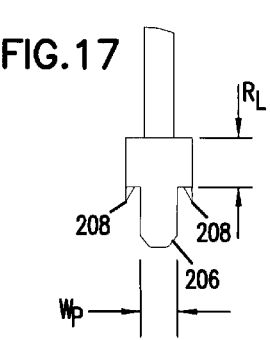
FIG.17

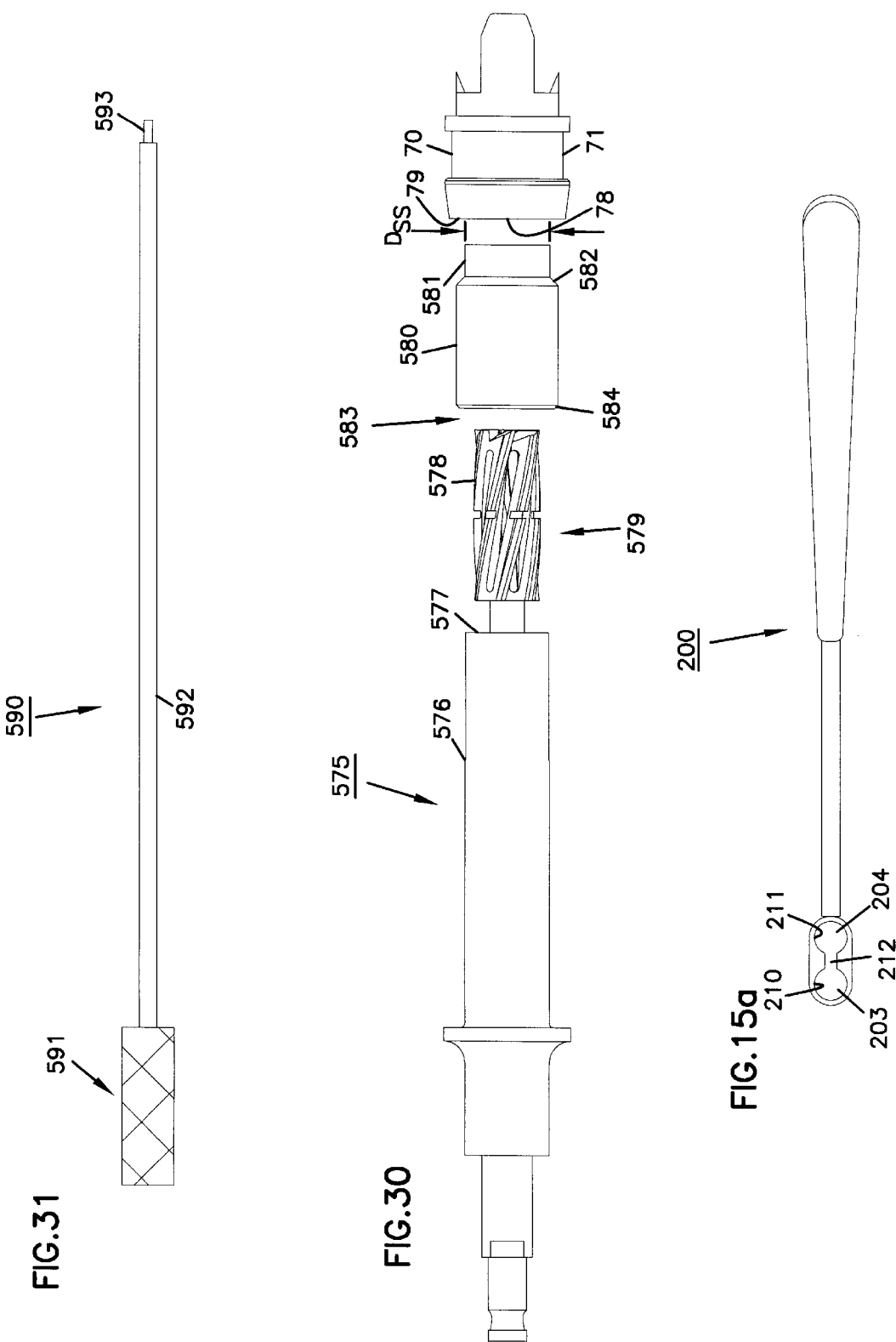

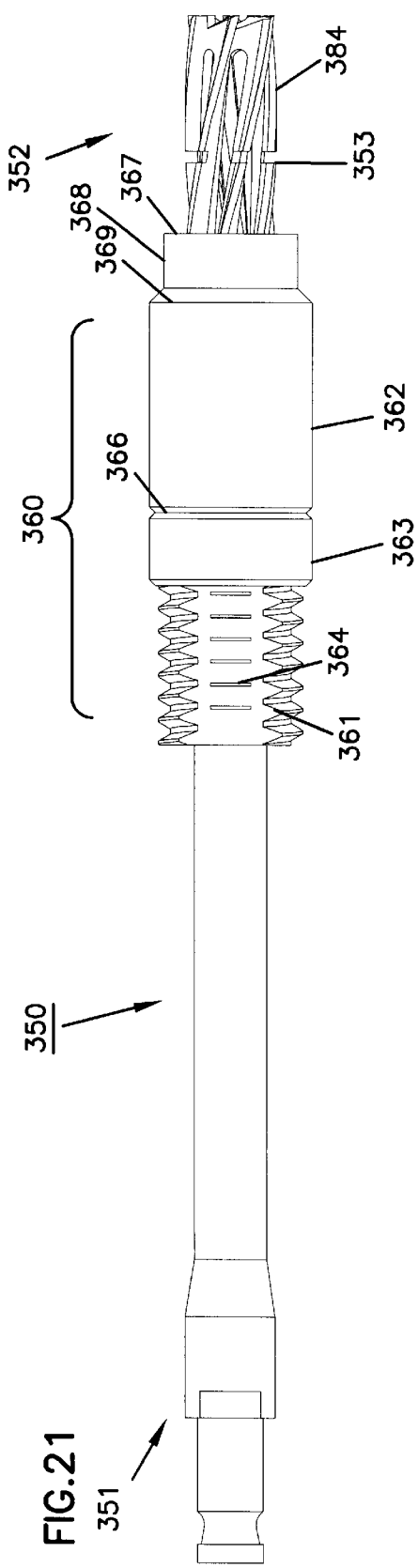
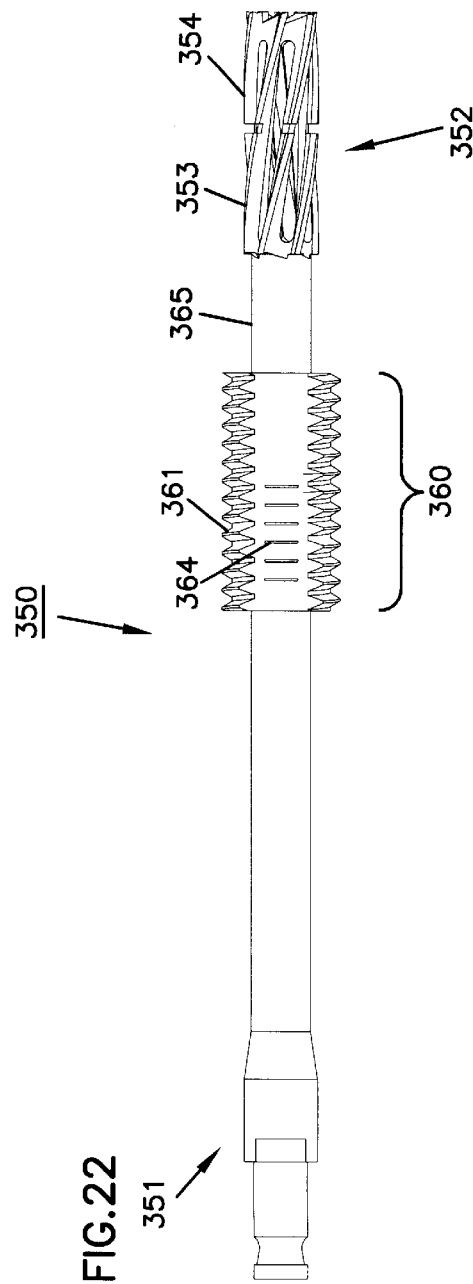

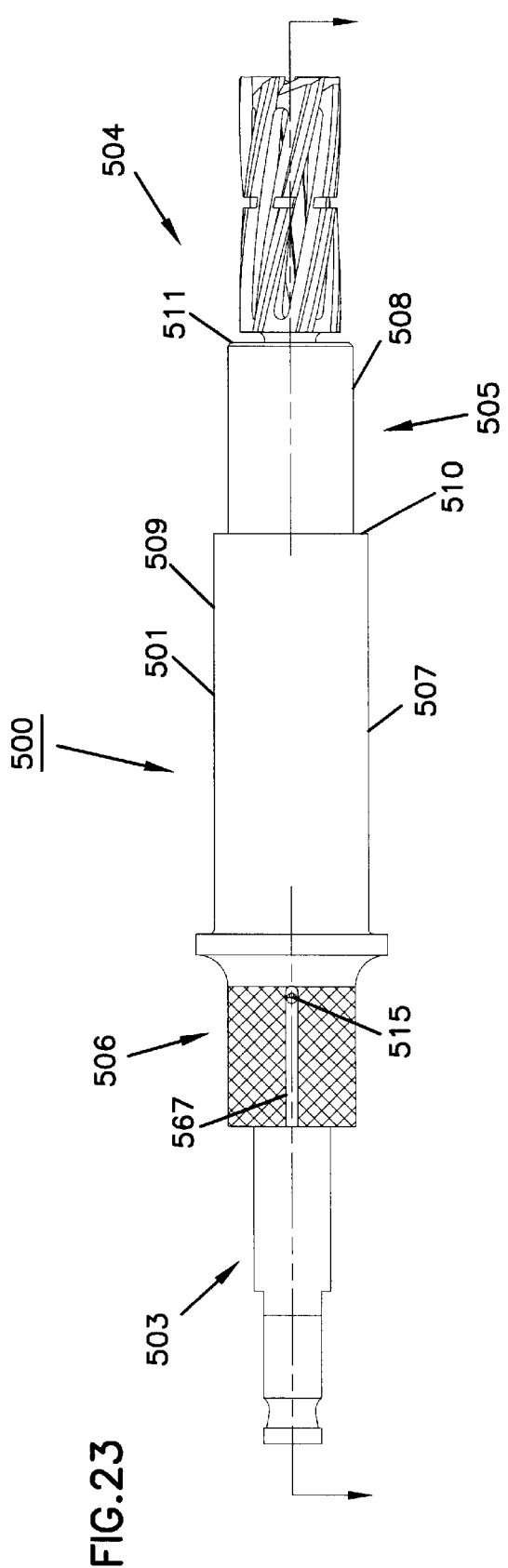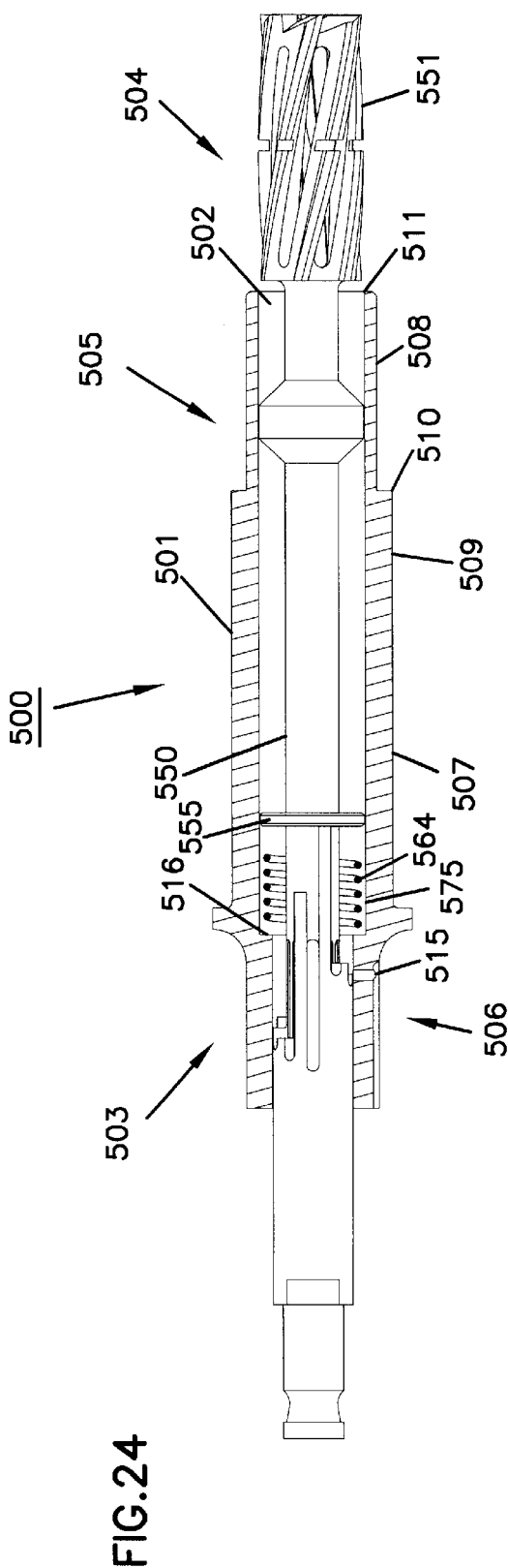
FIG.23
FIG.24

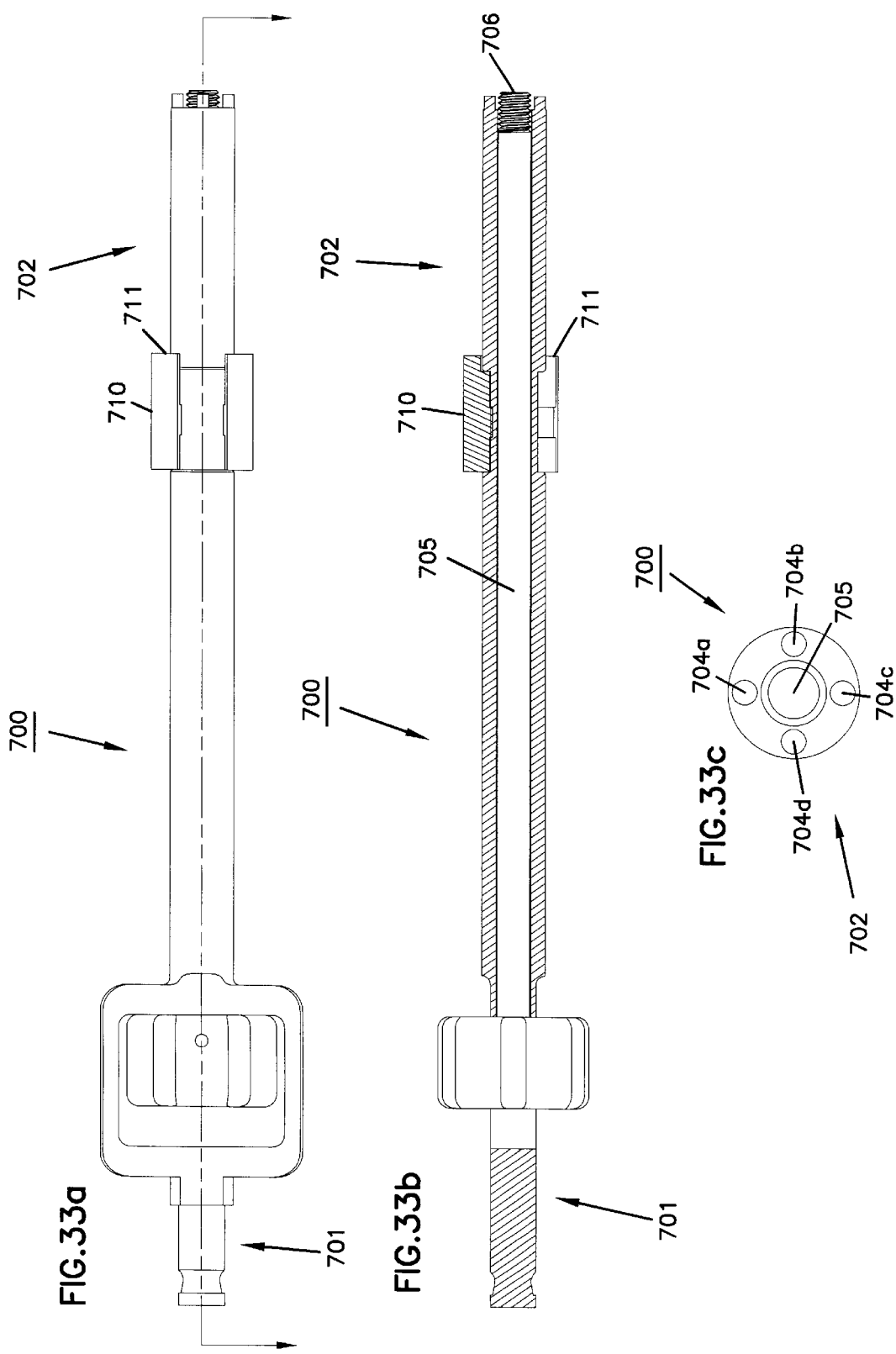

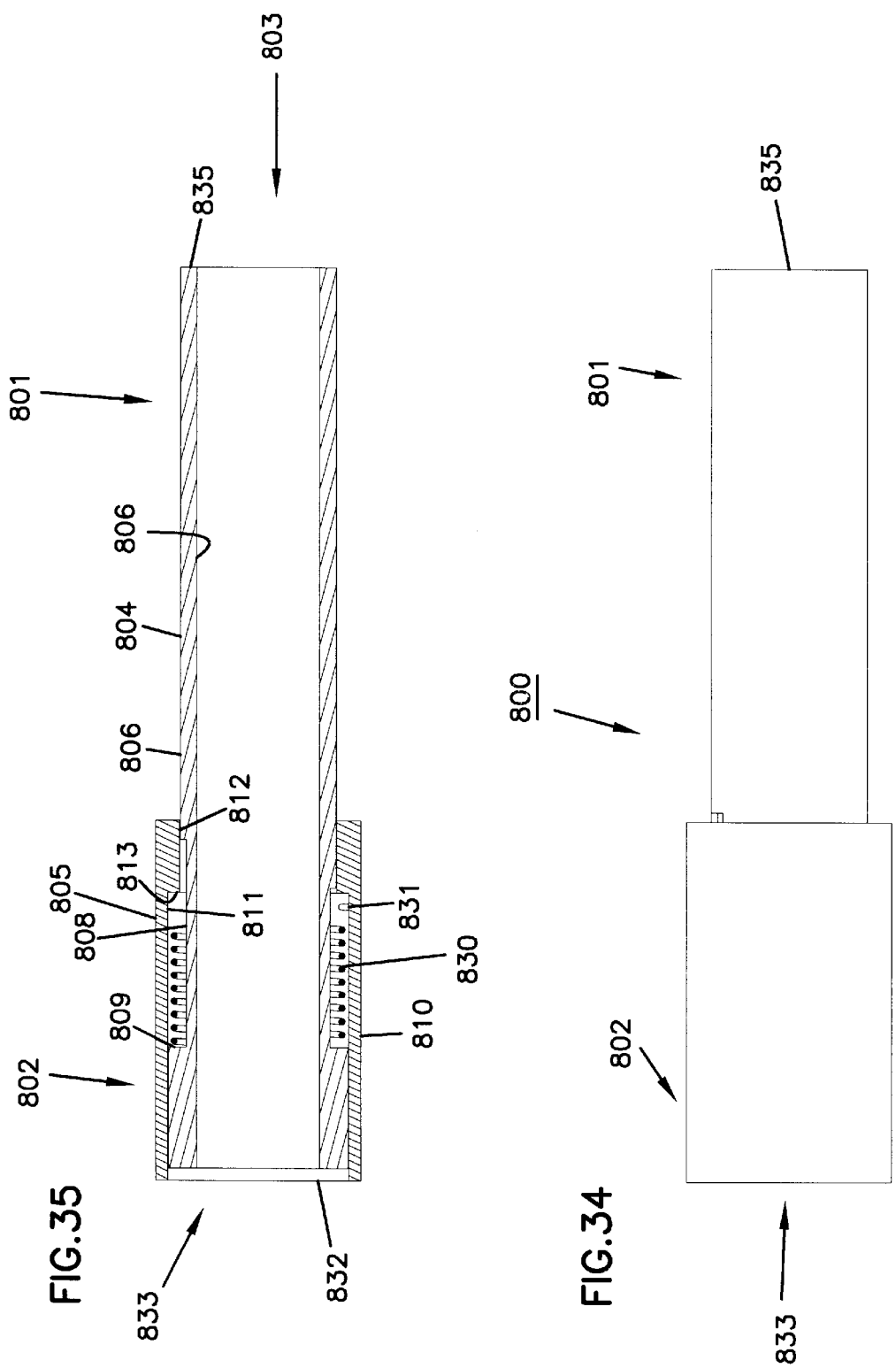

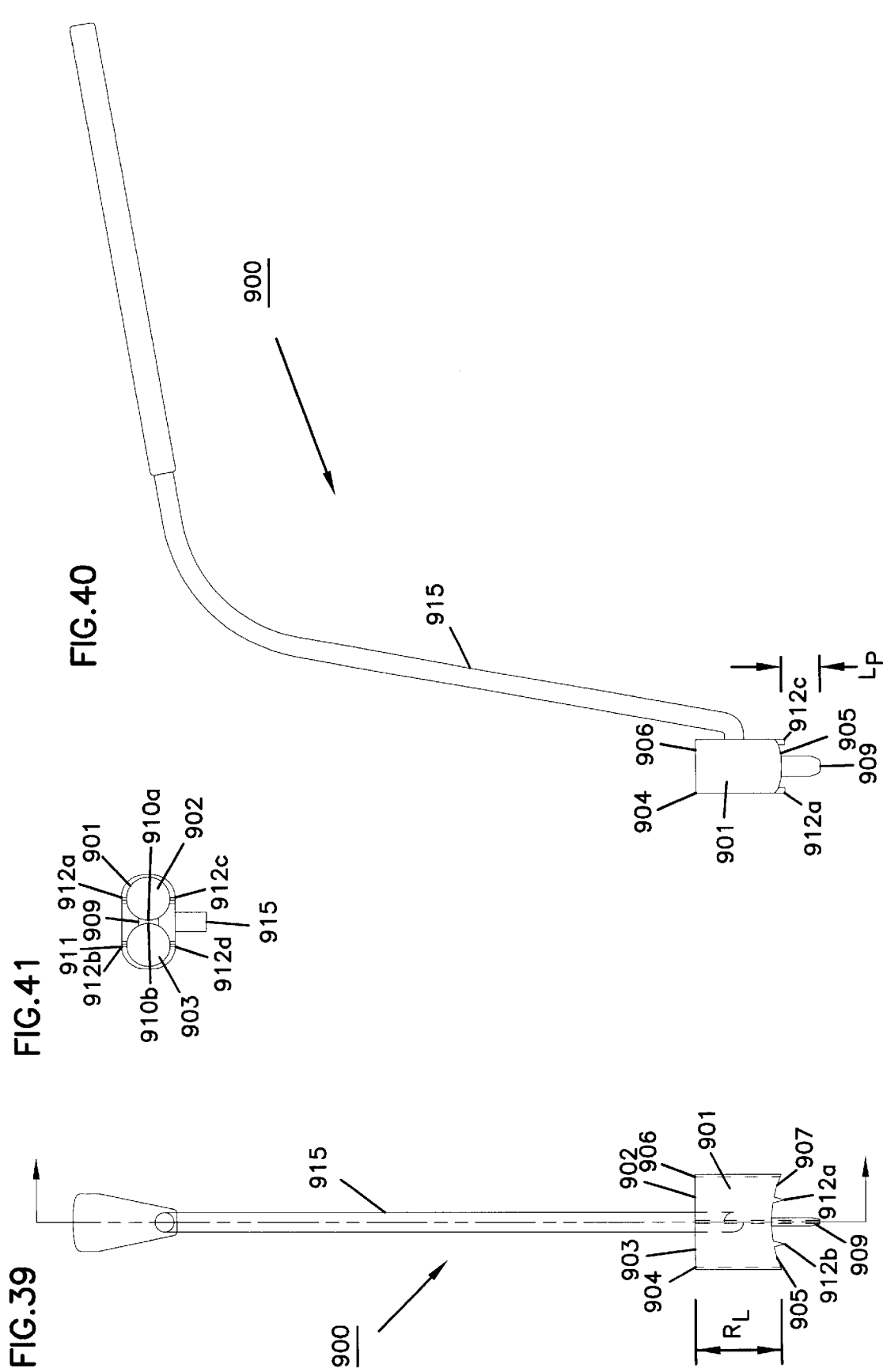

SPINAL SURGERY INSTRUMENTS AND METHODS

CROSS-REFERENCE TO RELATED APPLICATIONS

The present application is a continuation-in-part of and claims priority to U.S. Ser. No. 09/420,070, filed Oct. 18, 1999, now abandoned, the entire disclosure of which is incorporated herein by reference.

FIELD OF THE INVENTION

The invention pertains to vertebral body fusion. Specifically, the invention is directed to instrumentation and methods for insertion of spinal implants between opposing vertebral bodies to facilitate fusion of the bodies.

BACKGROUND OF THE INVENTION

Chronic neck and back problems can cause pain and disability for a large segment of the population. Frequently, the cause of the pain is traceable to diseased disc material between opposing vertebrae. When the disc material is diseased, the opposing vertebrae may be inadequately supported, resulting in persistent pain.

Surgical devices and techniques have been developed for removing diseased disc material and fusing the joint between opposing vertebral bodies. Arthrodesis of the intervertebral joint can reduce the pain associated with movement of a joint having diseased disc material. Some fusion techniques involve removal of the diseased disc, drilling a bore for receiving a fusion implant into the bore and inserting the implant between the opposing vertebral bodies.

Spinal fusion implants and related surgical instruments for implanting a fusion device are known and disclosed in, for example, U.S. Pat. Nos. 5,741,253; 5,658,337; 5,609,636; 5,505,732; 5,489,308; 5,489,307; 5,484,437; 5,458,638; 5,055,104; 5,026,373; 5,015,247; and 4,961,740, the disclosures of which are incorporated herein by reference.

Procedures for fusing an intervertebral joint space include removing disc material and preparing a bore for placement of one or more implants in the disc space by removing bone from opposing vertebrae which are adjacent to the disc space. Currently two of the most common approaches for preparing the bore are free-hand preparation using a powered boring device and manual or powered boring through a hollow guide tube. Systems which provide for preparing the implant site bore through a hollow guide tube are described in, for example, U.S. Pat. Nos. 5,484,437 and 5,489,307. Preparing the implant site by passing instruments, such as reamers or taps, through a hollow guide tube advantageously provides an isolated surgical field with reduced chance of injury to tissues surrounding the surgical site.

However, free-hand preparation of the implant site and some of the available hollow guide tube systems often do not provide a means for ensuring that an equal amount of bone is removed from the adjacent vertebral bodies during formation of the bore. This is particularly true for current systems used to fuse cervical vertebrae. In addition to other problems, removal of unequal amounts of bone can result in over reaming of one vertebra relative to the adjacent vertebra. Also, free-hand preparation and most hollow tube systems do not adequately ensure that reaming of the bore is performed parallel to the vertebral endplates. Failure to ream parallel to the endplates and/or over reaming of the vertebral bodies can result in misplacement of the fusion device or subsidence of the joint space post operatively.

Moreover, many of the available hollow tubes presently used as guides are relatively long, some having lengths that can be 10 to 30 times greater than the diameter of the bore. This length obscures direct visualization of the surgical site and prevents the surgeon from being able to continuously monitor, and adjust as needed, during the reaming or tapping procedure. In addition, while some presently available hollow tubes include paddles for insertion into the disc space, the paddles typically are short relative to the length of the hollow tube (e.g., having a paddle length:tube length ratio of about 1:6 to 1:35). Long hollow tubes relative to short paddles can introduce a significant lever arm effect. In such arrangements, small movements at the proximal end of the hollow tube can significantly alter the trajectory of a reamer or other instruments guided by the hollow tube. In addition to hollow instrument guides, the precision and ease of use of the instruments which are passed through the guide can also affect surgical outcome.

Thus, there is a continuing need for greater precision, safety and ease of use of instrumentation used for placement of spinal fusion implants. The present invention is directed to addressing these needs.

SUMMARY OF THE INVENTION

The present invention is directed to increasing the ease and enhancing the precision of placement of spinal fusion implants between opposing vertebral bodies. In particular, the invention provides instruments and methods for performing a spinal surgical procedure through a hollow guide wherein the guide has a low lever arm effect and can provide greater visibility when the guide is placed over a surgical site.

The invention also provides novel instrument guides, implant gauges, guide starters, reamers, taps and other associated instruments which can be used alone or combined in a kit to perform a spinal surgical procedure. The principles underlying some of the adjustable features of the instruments of the invention may also be advantageously applied for use with prior art hollow guide systems.

Methods for implanting a spinal implant into a disc space between opposing vertebral bodies using instruments and kits of the invention are also disclosed.

BRIEF DESCRIPTION OF THE DRAWINGS

FIG. 1b is a side view of the spinal implant of FIG. 1a;

FIG. 1c is a trailing end view of the implant of FIG. 1a;

FIG. 2a is a top plan view of an implant gauge according to the invention;

FIG. 2b is a side view of the implant gauge of FIG. 2a;

FIG. 3 is a side view of one embodiment of a guide according to the invention;

FIG. 3a is a side view of an alternative configuration for the handle shown in FIG. 3;

FIG. 4 is a top view of the guide of FIG. 3;

FIG. 5 is a close up side view of the distal end of the guide of FIG. 3;

FIG. 6 is a front view of the guide of FIG. 5;

FIG. 7 is a side view of the distal end of an alternative embodiment of a guide according to the invention;

FIG. 8 is a front view of the guide of FIG. 7;

FIG. 9 is a side view of the distal end of an alternative embodiment of a guide according to the invention;

FIG. 10 is a front view of the guide of FIG. 9;

FIG. 11b is a side view of one embodiment of a removable handle which can be used with the guide of FIG. 11a;

FIG. 12 is an alternative embodiment of a guide according to the invention;

FIG. 13 is a diagrammatic view of the embodiment of a guide of FIG. 12 illustrating planes in which the first and second end of the guide reside in;

FIG. 14 is a side view of one embodiment of a dual lumen guide according to the invention;

FIG. 15 is a top view of the guide of FIG. 14;

FIG. 15a is a top view of an alternative embodiment of a dual lumen guide;

FIG. 16 is a close up side view of the distal end of the guide of FIG. 14;

FIG. 17 is a front view of the guide of FIG. 15;

FIG. 21 is a side view of one embodiment of a reamer according to the invention;

FIG. 22 is a side view of the reamer of FIG. 21 with the adjustable nut and lock nut removed;

FIG. 23 is a side view of an alternative embodiment of a reamer according to the invention;

FIG. 24 is a longitudinal cross section through the reamer of FIG. 23;

FIG. 30 is an alternative embodiment of a reamer according to the invention;

FIG. 31 is a side view of a cleaning probe of the invention;

FIG. 32b is a distal end view of the handle of FIG. 32a;

FIG. 33a is a side view of an implant driver suitable for the invention;

FIG. 33b is a longitudinal cross section through the implant driver of FIG. 33a;

FIG. 33c is a distal end view of the implant driver of FIG. 33b;

FIG. 34 is a side view of the adjustable guide tube;

FIG. 35 is a longitudinal cross section through the adjustable guide tube of FIG. 35;

FIG. 39 is a front view of an alternative embodiment of a dual lumen guide according to the invention;

FIG. 40 is a side view of the guide of FIG. 39; and

FIG. 41 is a bottom plan view of the guide of FIG. 39 with an incomplete handle.

DETAILED DESCRIPTION

Figure 1A:
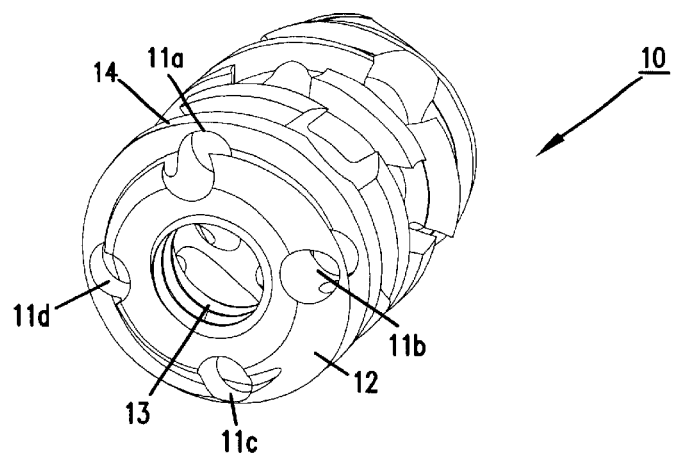
FIG. 1a is a perspective view of a spinal implant suitable for use according to the invention.

The present invention is directed to devices and methods which improve visualization and enhance the ease and precision of placement of spinal fusion implants between opposing vertebral bodies.

Throughout the specification, guidance may be provided through lists of examples. In each instance, the recited list serves only as a representative group. It is not meant, however, that the list is exclusive.

As used herein, the "depth" of a vertebrae is defined as the anterior posterior dimension of the vertebrae. The "width" of the vertebrae is the dimension from the right lateral edge to the left lateral edge. The "height" of the disc space is the dimension from the superior endplate to the inferior endplate of opposing vertebrae.

The instruments of the invention can be advantageously used for fusion of all types of joints. In some embodiments, the instruments and methods disclosed are particularly advantageous for preparing an implant site for fusing cervical vertebrae. Typical cervical vertebral joints fused are $C_2$–$C_3$ through $C_7$–$T_1$. Thus, for exemplary purposes, the invention will be described with reference to fusion of a cervical vertebral joint. However, it will be appreciated that the disclosed instruments and methods can also be used for fusion of vertebrae at other spinal locations.

The invention provides instruments, including guides, guide starters, implant depth gauges, reamers, taps and implant drivers and methods for preparing a spinal implant site. The invention also provides kits including instruments of the invention. Because the herein disclosed instruments are suitable for implanting various size implants, the kits can include multiple guides, starter guides, depth gauges, reamers, taps, etc. for different implant sizes.

A guide of the invention can be placed across an intervertebral joint space to facilitate placement and axial alignment of other instruments used to prepare a site for insertion of the implant between adjacent vertebrae. Accurate placement and alignment of instruments used to prepare the implant site helps reduce the chance of post-operative problems, including implant displacement, joint space subsidence, joint instability, non-union of the fusion site, etc. In general, the guide includes an external ring wall surrounding at least one lumen through which instruments can be passed for preparing the implant site. The lumen is defined by an internal ring wall. The internal ring wall, which can be complete or incomplete, also defines the diameter of the lumen.

The ring wall has a first ring wall length measured from a first end of the ring wall to a second end. In some embodiments, the ring wall has a second ring wall length, measured from the first end of the ring wall to the second end, which is different than the first ring wall length. Thus, in some embodiments the length of the ring wall is not the same around the circumference of the ring wall. However, in general, the greatest length of the ring wall preferably provides an aspect ratio of less than about 4:1. As used herein, "aspect ratio" refers to the ratio of ring wall length::lumen diameter. Thus, a ring wall with a 4:1 aspect ratio has a ring wall length that is four times the diameter of the lumen. In preferred embodiments, the aspect ratio is about 0.5:1 to 3:1 typically about 0.8:1 to 1:2.5. In some embodiments, the guide can include dual-lumens for placement of two implants in parallel alignment. In such embodiments, the external ring wall can surround both lumens with each lumen having separate internal ring walls. Typically, each lumen of a dual-lumen guide has an aspect ratio within the above stated ranges of aspect ratios.

In some preferred embodiments, the guide includes one or more projections or paddles extending from an end of the ring wall. Typically, the guide includes two diametrically opposed paddles which have a projection length extending from the first end of the ring wall to the end of the paddle. However, in some dual lumen guides, a single paddle located between the lumens may be used. In addition to other features, the paddles can advantageously maintain distraction of the disc space, enhance stabilization of the guide within the joint space and facilitate removal of equal amounts of bone from the vertebrae during reaming. Unlike prior art paddles, the length of the paddles of the present guides are preferably selected such that the length is greater than 50% of the depth the vertebrae between which the guide is placed. In addition, the length of the paddles are selected to reduce the lever arm effect of prior systems. Thus, in most embodiments, the length of the paddles, relative to the ring wall length (i.e., paddle length:ring wall length) can be reduced to about 1:4 to 3:1. Typically, the ratio of paddle length:ring wall length can be about 1:3 to 3:1, and, in preferred embodiments, about 1:1 to 1:2.5.

The width of the paddles among different guides can vary. In some embodiments, the inner surface of the paddles is arcuate and defines a radius of curvature substantially equal to the radius of curvature of the lumen. For a particular application, the width of the paddles, throughout a major portion of the length of the paddles, can be selected to correspond to the height of the distracted disc space. The paddle width can also vary from the proximal to distal aspect of the paddle. For example, a paddle can be convergently tapered from a proximal aspect to a distal aspect of the paddle to facilitate ease of insertion into an intervertebral space. The distal most aspect of a tapered paddle can further include a more acute taper to facilitate initial insertion into the disc space. A taper of the distal most aspect of a substantially non-tapered paddle can also be advantageously used.

In some embodiments, the length dimension of the paddle can be parallel to an axis passing through the lumen of the guide. In other embodiments, the length dimension of the paddles can converge towards, or, more likely, diverge away from an axis passing through the lumen of the guide. In still other embodiments, the distance between opposing paddles can be greater than the diameter of the lumen of the guide.

In general, multiple guides will be available which have paddles with varied widths. For cervical applications, a typical range of paddle widths is approximately 2 mm to 12 mm, in 1 mm increments. For a given guide, the paddle width is preferably about 1 mm to 3 mm less than the minor diameter of the implant to be inserted at the site prepared with the guide.

The paddles can be inserted into the disc space after distraction of the disc space or the paddles can be used to distract and maintain the distracted disc space. By selecting a paddle having a maximum width equal to the desired disc space height, the paddles can maintain distraction of the disc space during implant site preparation. In addition, due to the length of the paddles relative to the ring wall length, the paddles of the present guides provide increased stabilization of the guide to reduce the likelihood of movement during implant site preparation and further facilitate preparation of an implant site that is parallel to the joint space with substantially equal amounts of bone removed from the adjacent vertebral endplates.

The guide can also include an anchoring arrangement to anchor the guide to the vertebral bodies and a handle for holding and manipulating the guide. Suitable anchoring arrangements include one or more teeth, pins, tines, etc., which can penetrate into the vertebral body. The handle can be fixed or removable from the guide.

A guide starter can be used for placement of the guide in the intervertebral space. In general a portion of the guide starter can be positioned within a lumen of the guide and provide for substantially equal pressure to be applied around the circumference of the ring wall during placement of the guide in the disc space. As will be described, preferably, the starter guide includes a shoulder which can seat on an edge of the ring wall to apply equal pressure around the ring wall when the guide is placed into the disc space.

Novel implant gauges, reamers, taps, implant drivers and other instruments which are suitable for use according to the invention are also described. In one embodiment, the invention provides reamers and taps which are adjustable for selectively controlling reaming and tapping to predetermined depths. As will be further described, selective control can be provided by incremental stops which can be fixed for a particular instrument or selectively predetermined by the user. It will be appreciated that many of the principles disclosed herein for selective control of reaming and tapping depths can be applied to known hollow guide tubes to provide hollow guide tube systems which provide selective control of depth of penetration into a disc space when used with known reamers, taps, etc.

DETAILED DESCRIPTION OF THE ILLUSTRATED EMBODIMENT

The invention will be described with reference to the accompanying drawings, wherein like reference numerals identify similar or corresponding components throughout the several views. The illustrated embodiments and description are for exemplary purposes to facilitate comprehension of the invention and should not be construed to limit the scope of the invention. In addition, for purposes here, the invention will be described with reference to insertion of a spinal implant into a cervical disc space between cervical vertebrae. However, it will be appreciated that many of the described instruments and procedures are also suitable for insertion of implants at other intervertebral disc space locations.

Figure 1B:
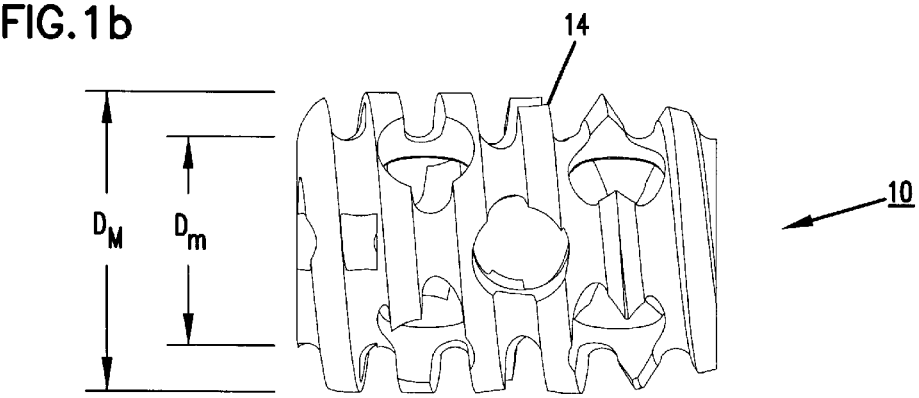
Figure 1C:
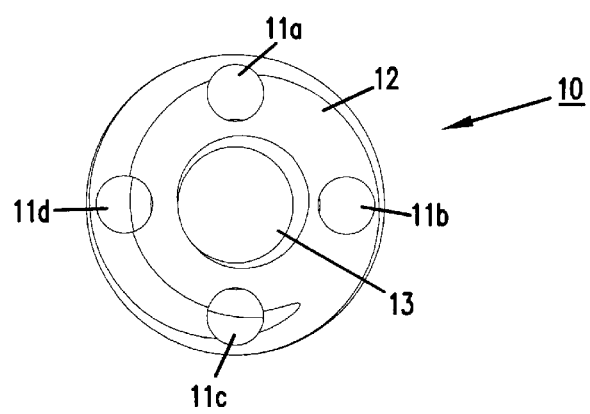

FIG. 1a illustrates a perspective view, FIG. 1b a side view and FIG. 1c a trailing end view of one example of a spinal implant 10 suitable for insertion in an intervertebral disc space using instruments and methods of the invention. Referring to FIG. 1b, $D_M$ is defined as the major diameter and $D_m$ is the minor diameter of implant 10. Implants having various diameters, lengths, thread patterns, etc., are available and can be used in accordance with the invention. Examples of sizes of the minor diameter $D_m$ of an implant for use in cervical fusions are 6 mm, 8 mm, 10 mm and 12 mm. The major diameter $D_M$ is typically 2–3 mm greater than the minor diameter $D_m$. The instruments of the invention can be sized for a particular size of implant.

FIG. 2a is a top plan view and FIG. 2b is a side view of an embodiment of an implant gauge 20 for measuring the disc height of an intervertebral disc space. In some embodiments, the minor diameter $D_m$ of an implant 10 is selected to be approximately 2–3 mm greater than the measured disc height. X-ray, CT or MRI films can be used to determine the size of an implant to be used at a particular location.

Implant gauge 20 includes a first end 21 and second end 22. First end 21 includes two measuring regions, a distal first end region 23 having a height $D_{H1}$ and a proximal first end region 24 having a height $D_{H2}$. The second end 22 also includes two measuring regions, a distal second end region 25 having a height $D_{H3}$ and a proximal second end region 26 having a height $D_{D4}$. Additional measuring regions can also be included. Other markings, for example measurement guide 27, can be present on gauge 20 for the surgeon's convenience. As will be described below, implant gauge 20 can be used to determine the disc space height of an intervertebral joint space to be fused. A kit of the invention can include multiple implant gauges having varied end region heights for measuring a range of disc heights. Typically, for cervical vertebral fusions the range of heights of the end regions which will be used for measuring disc space height which can be in 1 mm increments from about 2 mm to about 12 mm.

FIG. 3 is a side view of one embodiment of a guide 30 according to the invention. In this embodiment, guide 30 includes a ring wall 31 having a first end 32 and a second end 33, projections 34 and anchoring arrangement 35. Handle 36 comprises a proximal portion 37 and a distal portion 38 which is mounted to ring wall 31.

FIG. 4 is a top plan view illustrating that ring wall 31 has an internal ring wall 40 which defines a lumen 41 having a diameter $D_I$. In some preferred embodiments, to prepare an implant bore for an implant having a minor diameter $D_m$ lumen 41 is selected such that the $D_I$ equals $D_m$. In the illustrated embodiment, ring wall 31 of guide 30 is complete. However, in alternative embodiments, ring wall 31 need not be complete around the circumference of the ring wall. The wall thickness of ring wall 31 provides a first end edge 42 and a second end edge 43. The second end edge 43, is also referred to as the proximal edge.

Referring again to FIG. 3, distal portion 38 of handle 36 forms an angle α of about 0° to 30° with axis $A_L$ passing through lumen 41. The angle α between axis $A_L$ and distal portion 38 facilitates visualization of the surgical site. FIG. 3a illustrates an alternative configuration for handle 36. In other embodiments, the handle can be malleable to allow the surgeon to adjust the angle as necessary for a particular procedure. Also, it will be noted that in the embodiments of FIGS. 3–6, handle 36 is positioned relative to projections 34 such that when projections 34 are inserted into the disc space handle 36 is oriented perpendicular to the axis of the spine. However, in alternative embodiments, handle 36 can be oriented relative to paddles 34, such that when paddles 34 are inserted into the disc space, handle 36 is substantially parallel to the axis of the spine. Handle orientations between perpendicular and parallel can also be used.

Referring to FIGS. 3, 5 and 6, guide 30 will be further described. FIG. 5 is an enlarged side view of ring wall 31 and FIG. 6 is a front view rotated 90° from the view of FIG. 5 (i.e., viewed from opposite handle 36).

Projections 34 comprise opposing paddles 50 and 51 which extend from the first end 32 of ring wall 31. In the illustrated embodiment, anchor arrangement 35 comprises teeth 52, 53 to anchor guide 30 to the vertebral bodies. The width $W_P$ of paddles 50 and 51 can vary. However, in preferred embodiments, width $W_P$ of paddles 50 and 51 is selected to be substantially equal to the disc height determined with implant gauge 20. The paddle length $L_P$ of paddles 50 and 51 is preferably at least 50% of the depth of the vertebral bodies adjacent the intervertebral disc space to be fused.

As discussed above, the paddle length $L_P$ is selected to reduce the lever arm effect of prior systems. In the embodiment of FIGS. 3–6, ring wall length $R_L$ is the same around the entire ring wall 31. Also, paddle length $L_P$ is equal to lumen diameter $D_I$ and both are greater than ring wall length $R_L$.

FIGS. 7 and 8 illustrate an alternative embodiment of a guide 30 having a ring wall 31 wherein the ring wall length $R_L$ is the same around the entire ring wall 31 and ring wall length $R_L$ is equal to lumen diameter $D_I$, both of which are less than paddle length $L_P$.

FIGS. 9 and 10 illustrate another embodiment of a guide 30 having a ring wall 31 wherein ring wall length $R_L$ is the same around the entire ring wall 31 and ring wall length $R_L$ is greater than lumen diameter $D_I$ and both are less than paddle length $L_P$.

Figure 11A:
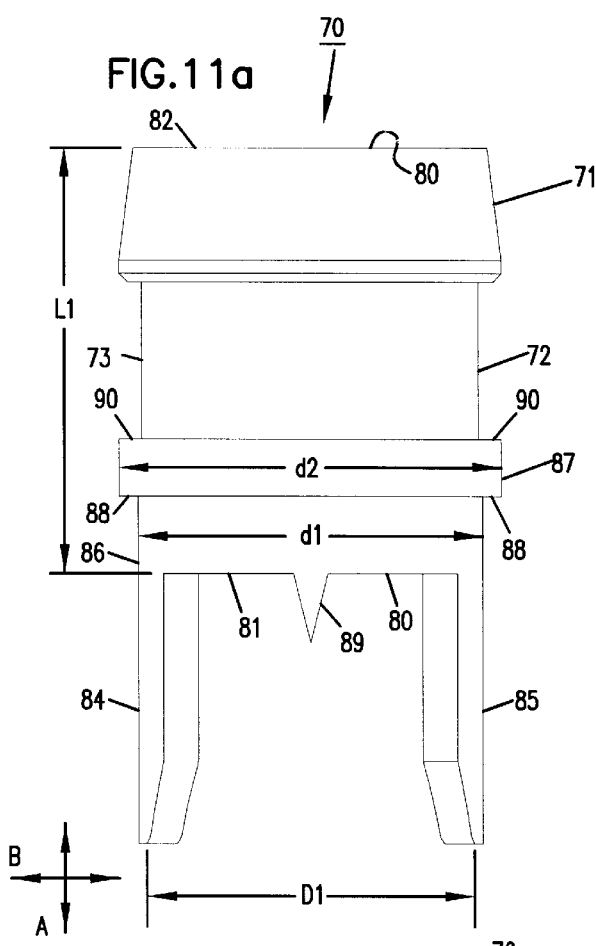
FIG. 11a is one embodiment of a guide according to the invention having a removable handle and shown without a handle.
Figure 11D:
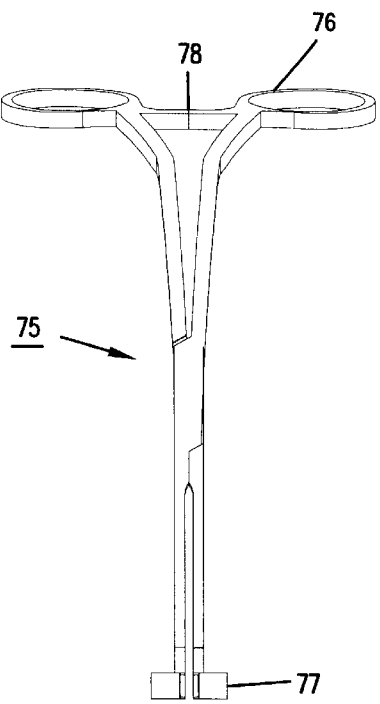
FIG. 11d is a front view of the handle of FIG. 11b.
Figure 11B:
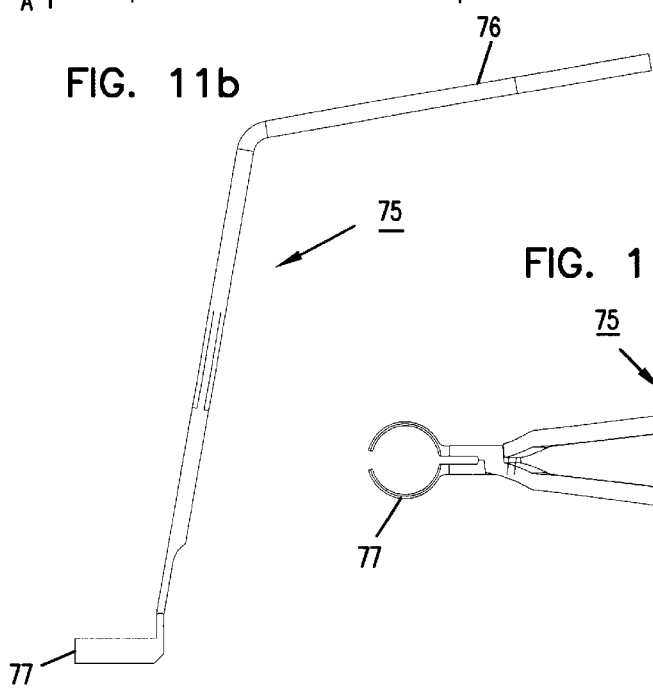
Figure 11C:
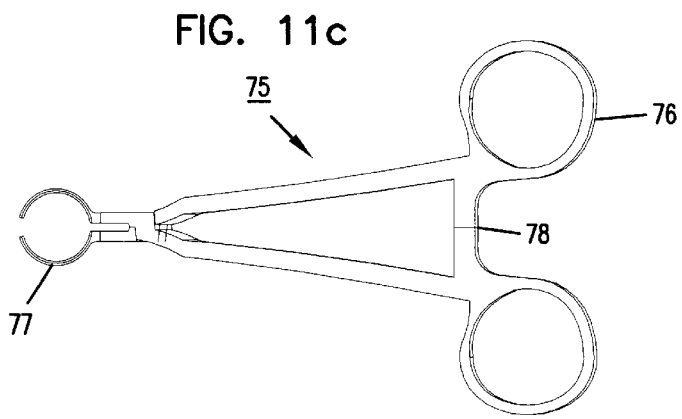
FIG. 11c is a top plan view of the handle of FIG. 11b.

FIG. 11a illustrates an alternative embodiment of a guide 70 wherein ring wall 71 has an exterior surface 72 including a groove 73 for cooperatively mounting to a removable handle 75 such as illustrated in FIGS. 11b–d. As illustrated, handle 75 includes a proximal end 76 for operating handle 75 and a distal end attachment 77 for mounting the handle 75 to the guide 70. The size of the opening of distal end attachment 77 can be locked into a selected position by use of, for example, known ratchet locking systems 78.

The ring wall 71 of guide 70 has a ring wall length L1 that extends between a first end 81 and a second end 82 measured along a first orientation A. The guide embodiment 70 shown in FIG. 11a further includes a window 80 that extends through the ring wall 71 from the first end 81 to the second end 82 of the ring wall. The window 80 has an opening dimension D1 measured along a second orientation B. The opening dimension D1 of the window 80 extends between opposing paddles 84 and 85. As previously described, the ratio of the ring wall length L1 to the window opening dimension D1 is less than about 4:1.

The ring wall 71 also includes a first portion 86 and a second portion 87. The second portion 87 is located adjacent the groove 73. The first portion 86 is located adjacent the second portion 87. In the depicted embodiment, the first portion 86 and the second portion 87 adjoin at a shoulder 88. The second portion 87 defines a handle engagement surface 90. The handle engagement surface 90 faces opposite the paddles 84, 85 and engages the handle 75 when the handle is mounted in the groove 73.

The first portion 86 has a first outer dimension d1 measured along the second orientation B. The second portion 87 has a second outer dimension d2 measured along the second orientation B. In the illustrated embodiment, the second outer dimension d2 is greater than the first outer dimension d1.

The paddles 84, 85 are located adjacent the first portion 86 of the ring wall 71. The paddles 84, 85 project outwardly from the first end 81 of the ring wall 71 along the first orientation A. As described previously, the paddles are sized for insertion between opposing vertebral bodies to separate the vertebral bodies during the spinal implant procedure.

The guide 70 of FIG. 11a further includes at least one tooth 89. The depicted anchoring tooth 89 is located adjacent the first portion 86 at the first end 81 of the ring wall 71. The anchoring tooth 89 projects outwardly from the first end 81 of the guide 70 along the first orientation A to penetrate the vertebral bodies when the opposing paddles 84, 85 are inserted between the vertebral bodies. In the illustrated embodiment, the tooth 89 is triangular in shape.

FIGS. 12 and 13 illustrate alternative embodiments of a guide 100 of the invention. As illustrated in FIG. 13, a plane $P_1$, passing through first end 101 of ring wall 103 forms an angle β with a plane $P_2$ passing through the second end 102 of ring wall 103. Thus, ring wall 103 has a first ring wall length $R_{L1}$ measured from first end 101 to second end 102, which is greater than second ring wall length $R_{L2}$, measured from first end 101 to second end 102 at a point diametrically opposed to $R_{L1}$. The advantage of this configuration for some applications is discussed below.

FIG. 12 is a side view of guide 100 (handle not shown) showing paddle 105 (opposing paddle not visible in this view) inserted into intervertebral disc space IS between adjacent cervical vertebrae $C_X$ and $C_Y$. "A" indicates the anterior vertebral surfaces and "P" indicates posterior surfaces. As illustrated, within the cervical spinal region, the intervertebral disc space IS is generally not perpendicular to the anterior margins of the vertebral bodies. Also, the inferior end plate 150 of superior cervical vertebrae $C_X$ is typically concave. The superior end plate 151 of inferior cervical vertebrae $C_Y$ is typically flat to slightly concave.

The configuration of guide 100 facilitates boring an implant site substantially parallel to disc space IS and removal of equal amounts of bone from the opposing end plates 150, 151, during reaming when the end plates are not parallel and the disc space IS is not perpendicular to the vertebral margins. Creating a bore having a longitudinal axis parallel to the disc space facilitates removal of equal amounts of the endplate bone of opposing vertebrae and reduces the likelihood of, for example, post-surgical subsidence of the vertebrae.

Referring to FIG. 13, typically planes $P_1$ and $P_2$ form an angle β of about 0° to 30°, and in some preferred embodiments, about 5° to 20°. This angulation between the first end 101 and second end 102 of guide 100 ensures that a reamer passed into the lumen of guide 100 will be aligned to create an implant bore substantially parallel to the disc space IS. The elongate paddle length $P_L$ of paddle 105, relative to the depth of vertebrae $C_X$ and $C_Y$, reduces the likelihood of inadvertent displacement of the position of guide 100 by providing a small lever arm relative to ring wall length $R_L$ (or ring wall lengths $R_{L1}$, $R_{L2}$). In addition, the length $P_L$ of paddle 105, relative to the depth of vertebrae $C_X$ and $C_Y$, reduces the chances that the surface contours of the endplates 150, 151 will cause formation of an implant bore that is not parallel to the intervertebral disc space IS.

FIGS. 14–17 illustrate an alternative embodiment of a guide 200. FIG. 14 is a side view of guide 200 having a ring wall 201 including dual lumens 203 and 204. FIG. 15 is a top plan view showing that in the illustrated embodiment, the diameter $D_I$, of lumens 203 and 204 are equal. However, the lumen sizes need not be equal. As illustrated for some previous embodiments of a guide, guide 200 includes a handle 205, paddles 206, 207 and anchoring arrangement 208. In the illustrated embodiment, lumen diameter $D_I$, is less than ring wall length $R_L$ which is less than paddle length $L_P$. However, it will be appreciated that other lumen diameter, ring wall and paddle length sizes can be used as previously described.

FIG. 15a illustrates that in some embodiments, the internal walls 210, 211 of lumens 203, 204, respectively, need not be complete. Rather, a contiguous space 212 can exist between lumens 203, 204.

FIGS. 39–41 illustrate an alternative embodiment of a dual-lumen guide 900. FIG. 39 is a front view and FIG. 40 is a side view of guide 900 having an external ring wall 901 including dual lumens 902 and 903. The thickness of ring wall 901 provides a first edge 904 and a second edge 905. The first edge 904 is also referred to as a proximal edge 906. In the embodiment illustrated here the second edge 905 has a concave surface 907. Concave surface 907 can advantageously provide for the dual-lumen guide to more closely follow the curved contours of the vertebral bodies when in use.

Also in this embodiment, a single paddle 909 located between lumens 902 and 903 extends from second edge 905. Referring to FIG. 41, the bottom plan view shows that the paddle 909 includes bilateral concave surfaces 910a and 910b. In this embodiment, the concave surfaces 910a and 910b of paddle 909 have a curved radius which is the same as the radius of lumens 902 and 903. However, the concave surfaces need not have radiuses which are the same as the radius of the lumens. Moreover, it will be appreciated that although the bilaterally concave paddle surfaces 910a and 910b are advantageous in certain circumstances, a single central paddle such as paddle 909 having non-concave surfaces (e.g., linear) could also be used.

Guide 900 can also include an anchoring arrangement 911 comprising teeth 912a–912d (or other previously described anchoring arrangement) extending from second edge 905. Guide 900 can also include a handle 915. Handle 915 can be positioned relative to the external ring wall 901 in any of the various positions previously discussed for other embodiments of the invention. In addition, the length of the ring wall and paddle relative to one another and relative to the lumen diameters can vary as described for other embodiments of the invention.

As previously described, paddle 909 can be inserted into the disc space after distraction of the disc space or the paddle can be used to distract and maintain the distracted disc space. By selecting a paddle width equal to the desired disc space height, the paddle can maintain distraction of the disc space during implant site preparation. As with other embodiments of the invention, due to the length of the paddle relative to the ring wall length, the paddle provides increased stabilization of the guide to reduce the likelihood of movement during implant site preparation and can facilitate preparation of an implant site that is parallel to the joint space.

Typically, a dual lumen guides can enhance the accuracy of parallel alignment between two implants inserted into the intervertebral disc space by providing early and continued maintenance of parallel operating fields at both implant sites.

Figure 19:
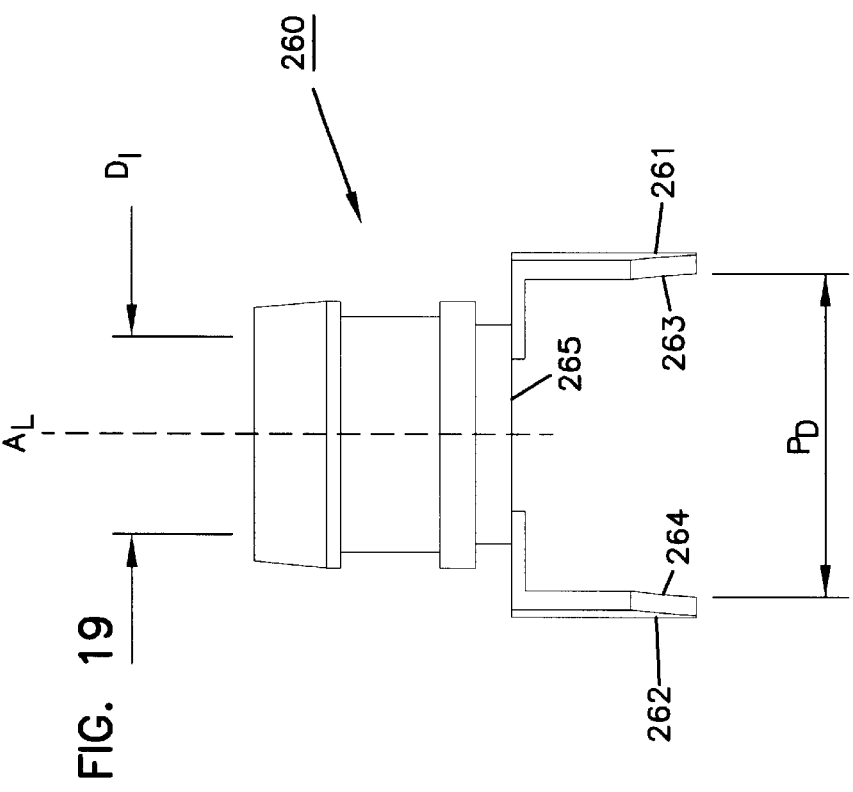
FIG. 19 is a side view of an alternative embodiment of a guide according to the invention.
Figure 18:
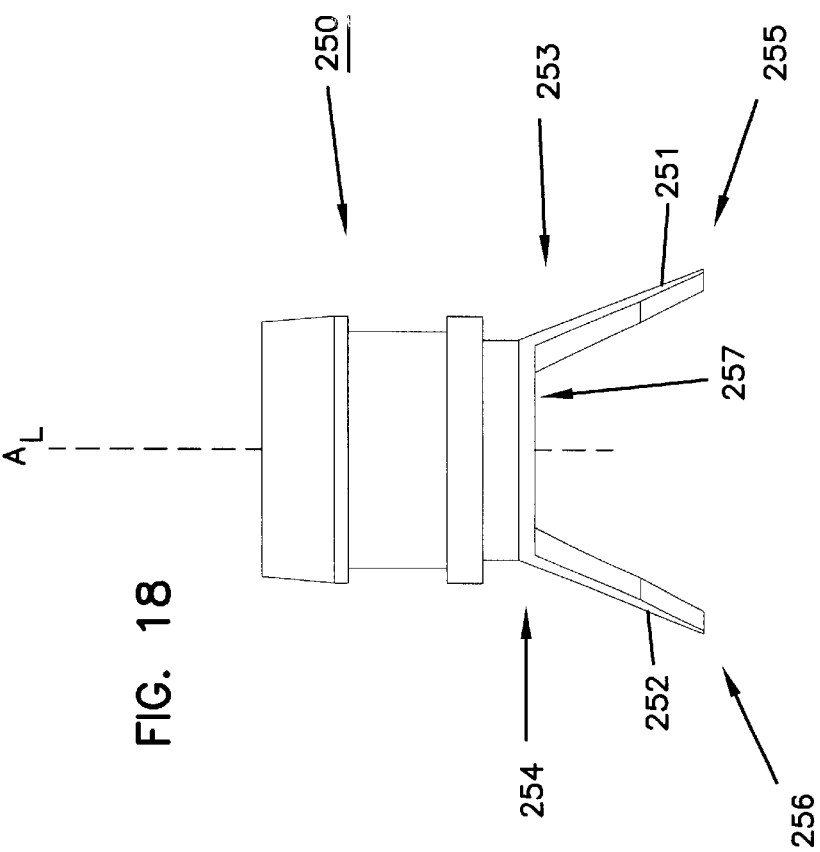
FIG. 18 is a side view of an alternative embodiment of a guide according to the invention.
Figure 19A:
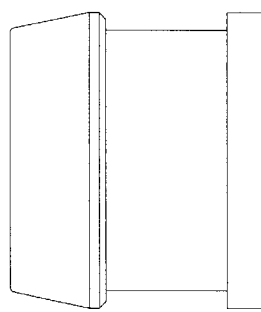
FIG. 19a is a side view of an alternative embodiment of a guide according to the invention.

FIGS. 18, 19 and 19a illustrate additional embodiments of a guide 250, 260 and 270. FIG. 18 illustrates that guide 250 includes paddles 251 and 252 which diverge away from axis $A_L$ of lumen 257 from the proximal end 253, 254, to the distal end 255, 256 of paddles 251, 252, respectively. In FIG. 19, the distance $P_D$, between the interior surfaces 263, 264 of paddles 261, 262, respectively, is greater than the diameter $D_I$, of lumen 265 of guide 260. The configurations of FIGS. 18 and 19 can advantageously provide greater retraction of soft tissue structures away from the surgical field within lumens 257, 265.

The guide 270 of FIG. 19a illustrates paddles (only one visible) having a taper. That is, the width at the proximal end 272 ($W_{P272}$) of paddle 271 is greater that the width at the distal end 273 ($W_{P273}$). The tapered configuration of paddle 271 facilitates use of guide 270 to more easily be passed into and distract an intervertebral disc space. For any specific procedure, the width of paddle 271 at the proximal end 272 ($W_{P272}$) can be selected to provide the selected height of a distracted disc space. According to the invention, a guide having paddles tapered as for guide 270 can also include any of the previously described features of a guide as well as additional paddle configurational features shown for other guides including, for example, those illustrated in FIGS. 3–5, 7–10, 11a–19, 39–41, etc.

Figure 20:
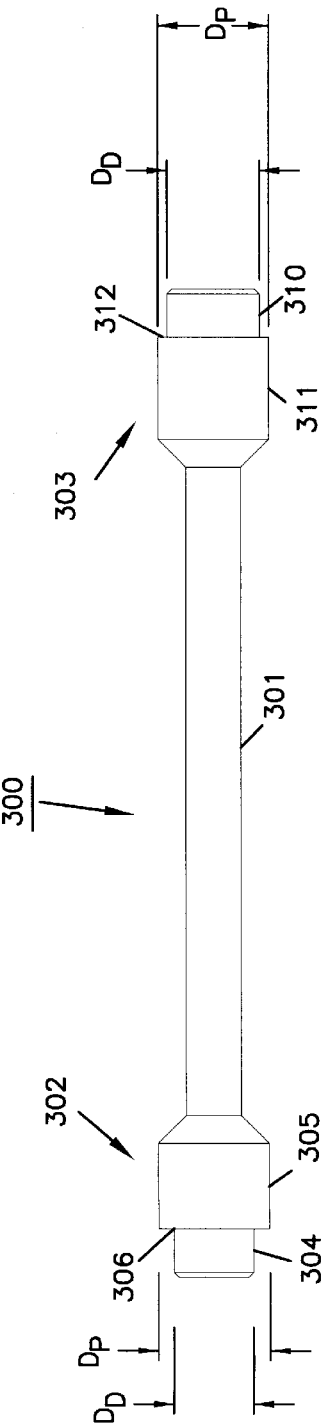
FIG. 20 is a side view of an embodiment of a guide starter according to the invention.

FIG. 20 is a side view of a guide starter 300 according to the invention. Guide starter 300 includes a starter shaft 301 having a first end 302 and second end 303. First end 302 includes a distal end region 304 having a distal end region diameter $D_D$ and a proximal end region 305 having a proximal end region diameter $D_P$. The junction of distal end region 304 and proximal end region 305 form a shoulder 306. Distal end region diameter $D_D$ is sized to fit within a guide lumen (e.g., 41 of FIG. 4) such that shoulder 306 rests on proximal edge 43 (FIG. 4) of ring wall 31. Thus, by tapping on second end 303, shoulder 306 provides for substantially equal pressure to be applied around the circumference of ring wall 31 to force the paddles (e.g., 50, 51) of a guide (e.g., 30, 100, 200) into the intervertebral disc space. It will be appreciated that the second end 303 of guide starter 300 can also include a distal end region 310 and a proximal end region 311 to form a shoulder 312. Each distal and proximal end regions having a different diameter. Multiple guide starters each having different size distal and proximal region diameters can be provided in a kit to match guides having corresponding lumen diameters.

FIGS. 21 and 22 illustrate one embodiment of an adjustable reamer suitable for use according to the invention. Adjustable reamer 350 includes a proximal end 351, and a distal end 352 having a working end 353 comprising a cutting end 354 for reaming an implant bore between adjacent vertebrae. In the illustrated embodiment, the bore depth of reamer 350 can be selectively adjusted to a predetermined depth by adjustment arrangement 360 comprising threads 361, adjustment nut 362 and lock nut 363.

Referring to FIG. 22, adjustment nut 362 and lock nut 363 have been removed to show that reamer 350 also includes a proximal shaft region 365 providing spacing between cutting end 354 and adjustment threads 361. Adjustment threads 361 provide for threadedly moving locking nut 363 to a selected position which can be guided by, for example, depth markings 364. In the illustrated embodiment, depth markings 364 correspond to a particular implant bore-depth. The position of adjustment nut 362 can be fixed by threading adjustment nut 362 against the distal end 366 of lock nut 363. In use, the depth of reaming is controlled by the affirmative stop which occurs when the distal edge 367 of adjustment nut 362 contacts the proximal edge of a ring wall (e.g., 43 of FIG. 4). In an alternative embodiment, the diameter of the distal end region 368 of adjustment nut 362, can be sized to fit within the lumen of the guide such that contact of lip 369 with proximal edge 43 of the guide affirmatively stops the depth of reaming.

Figure 25:
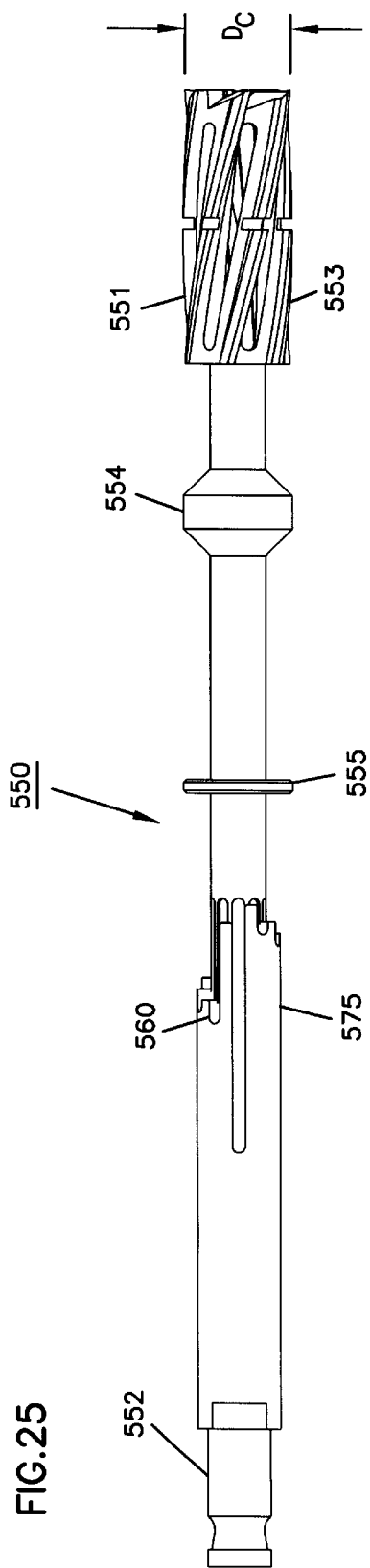
FIG. 25 is a side view of a shaft of the reamer of FIG. 23.

FIGS. 23–26 illustrate an alternative embodiment of an adjustable reamer 500 according to the invention. Referring to FIGS. 23–25, adjustable reamer 500 includes a proximal end 503, a distal end 504, a tubular sleeve 501 and a shaft 550 in the lumen 502 of tubular sleeve 501.

Tubular sleeve 501 has a first end 505 and a second end 506. In the illustrated embodiment, wall 507 of tubular sleeve 501 has a first outer diameter 508 and a second outer diameter 509 forming lip 510 at first end 505. In use, lip 510 acts to affirmatively stop the passage of reamer 500 through the lumen 41 of ring wall 31 (e.g., FIG. 4) when the proximal lip 510 of reamer contacts the proximal edge 43 of ring wall 31. However, (as discussed and illustrated below with the discussion of a tap) in an alternative embodiment with an appropriate size guide lumen, distal edge 511 can also act as an affirmative stop. When using a reamer 500 having a tubular sleeve 501 configured to include a lip 510, the lumen 41 diameter $D_I$, of a guide 30 is selected such that diameter $D_I$, is of a size sufficient to permit passage of first outer diameter 508 into lumen 41.

Referring now to FIG. 25, shaft 550 includes a working end 551 and an operating end 552. Working end 551 comprises a cutting head 553.

The diameter $D_C$ of cutting end 553 is sized to permit passage into lumen 502. In use, $D_C$ is typically selected to equal $D_m$ of implant 10. Thus, according to this embodiment, the diameter $D_I$, of lumen 41 of a guide 30 is selected for close tolerance passage of first outer diameter 508, rather than close tolerance with diameter $D_C$ of cutting end 553. A handle described below, can be mounted to the operating end 552 to rotate the shaft for boring an implant site with the cutting head 553. Shaft 550 can also include a stabilizer 554 for controlling lateral stability of shaft 550 when within lumen 502 of tubular sleeve 501. The function of fixed ring 555 is further described below. Shaft 550 also includes a portion of depth adjustment arrangement 575 having stops 560 and slots 561 which are seen in FIG. 25 and shown in laid out form in FIG. 26.

Figure 26:
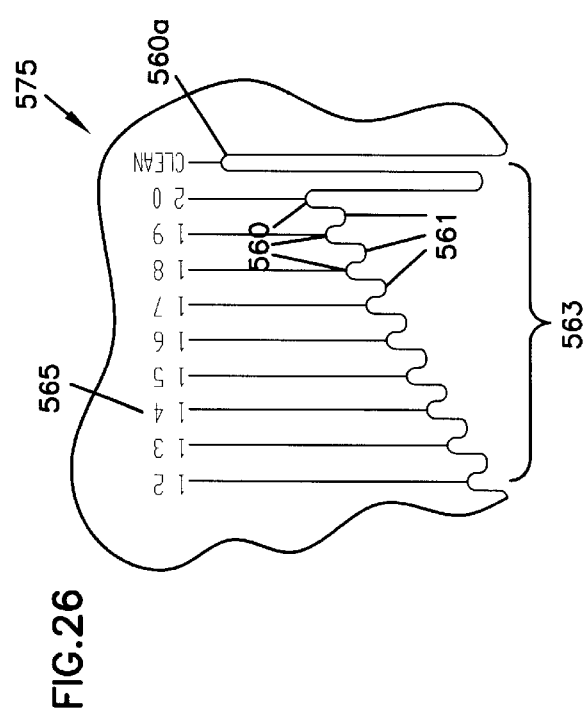
FIG. 26 is a laid-out view of an embodiment of stops for a depth adjustment arrangement suitable for the reamer of FIG. 23.

Referring to FIG. 26, it will be appreciated that stops 560 are positioned an incremental distance from cutting end 553 (and first end 505 of tubular sleeve 501) and are the terminal point of slots 561. Each of the incremental positions of stops 560 correspond to an incremental position by which working end 551 can protrude from the first end 505 of tubular sleeve 501.

Referring again to FIG. 24, the operation of adjustable reamer 500 will be described. At the proximal end 503 of adjustable reamer 500, tubular sleeve 501 includes a pin 515 which passes into the lumen 502 of the second end 506 of tubular sleeve 501. The stair step arrangement 563 of stops 560 and slots 561 permits pin 515 to interdigitate with the slots 561 and contact stops 560 to fix the protrusion of cutting head 553 at a predetermined position beyond the first end 505 of tubular sleeve 501. Thus, by sliding tubular sleeve 501 towards the working end 551 of shaft 550, pin 515 can be advanced out of a particular slot 560 such that when tubular sleeve 501 is axially rotated pin 515 can be repositioned to pass into an alternative slot. Once rotated to a selected slot position, sleeve 501 can retract away from working end 551, and pin 515 can retract to the corresponding stop 560, by use of a biasing force, such as helical spring 564, to bias tubular sleeve 501 in a direction toward the proximal end 503 of adjustable reamer 500. Helical spring 564 provides a biasing force by acting against fixed ring 555 and shoulder 516 within lumen 502. Referring to FIG. 26, in the illustrated embodiment, stop 560a is positioned for convenient cleaning of adjustable reamer 500 by permitting tubular sleeve 501 to move a sufficient distance proximally to permit easy access to all aspects of cutting head 553.

Thus, positioning pin 515 against a selected stop 560 allows for selective positioning of working end 553 relative to shoulder 510 (or distal edge 511). The position of cutting head 553, relative to shoulder 510, determines the depth of an implant bore by controlling the depth of penetration of cutting head 553 into the disc space before the reamer is affirmatively stopped by proximal edge 43 of guide 30.

Referring to FIG. 23, in the illustrated embodiment, pin 515 is located in groove 567. Groove 567 can be positioned to align with numerical markings 565 (in FIG. 26), such that each numerical marking provides quick correlation of a particular bore depth to be used for a particular implant length.

After reading the foregoing discussion, it will be appreciated that alternative configurations for the pins, slots and grooves of the depth adjustment arrangement can be utilized and are within the scope of the invention.

Figure 27:
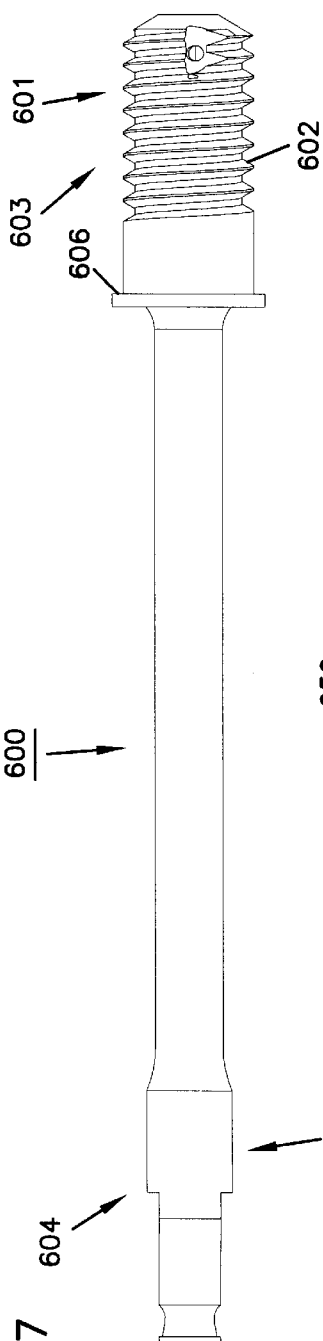
FIG. 27 is a side view of one embodiment of a tap suitable for use according to the methods of the invention.

In some procedures, it may be desirable to tap the implant bore prior to placement of an implant. FIG. 27 illustrates one example of a tap 600 suitable for the invention. According to this embodiment, tap 600 includes a working end 601, specifically a tapping head 602 at end 603 which is spaced a distance from an operating end 604 at proximal end 605. A handle can be mounted to operating end 604 for operating tap 600. Tap 600 also includes a lip 606 which can act as an affirmative stop to limit depth of tapping when lip 606 contacts proximal edge 43 of guide 30.

Figure 28:
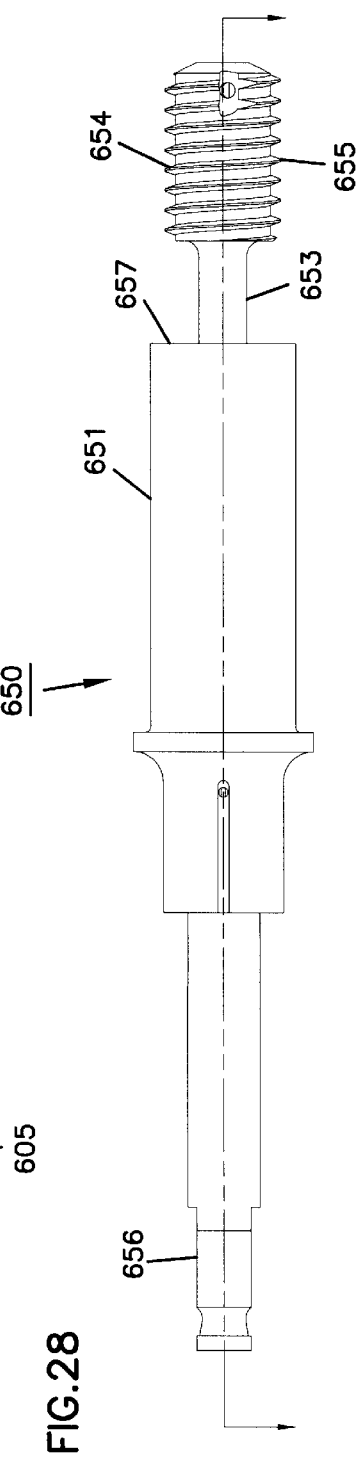
FIG. 28 is a side view of an embodiment of an adjustable tap according to the invention.
Figure 29:
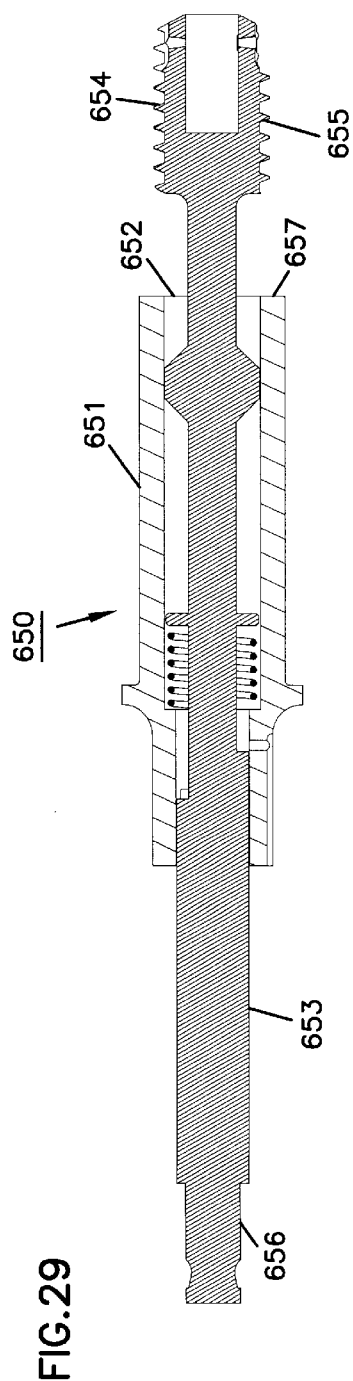
FIG. 29 is a longitudinal cross section view of the tap of FIG. 28.

Referring to FIGS. 28 and 29, in an alternative embodiment, a tap according to the invention can be an adjustable tap 650. Similar to adjustable reamer 500, adjustable tap 650 includes a tubular sleeve 651 having a lumen 652 through which is passed a shaft 653. Shaft 653 includes a working end 654 comprising a tapping head 655. The operating end 656 of shaft 653 can be configured for attachment to a handle as described below. Tubular sleeve 651 has a distal edge 657 which acts as an affirmative stop to the depth of tapping when it contacts the proximal edge 43 of guide 30. The components of a depth adjustment arrangement described for adjustable reamer 500 are also present in adjustable tap 650.

FIG. 30 illustrates a side view of an embodiment of an adjustable reamer similar to reamer 500 of FIGS. 23–26, but wherein the configuration of tubular sleeve 576 is similar to tubular sleeve 651 of tap 650 in FIGS. 28–29. That is, tubular sleeve 576 has a distal edge 577 and only a single outer diameter size at the distal end. One purpose of FIG. 30 is to illustrate another arrangement of a guide according to the invention which provides further selectivity for the surgeon. Specifically, in the event that a surgeon desires both the visibility advantage of a low profile ring wall, e.g., 71 of guide 70, and greater lateral support when reaming, spacing sleeve 580 can be used.

In the illustration of FIG. 30, spacing sleeve 580 includes a distal end region 581 having an outside diameter $D_{SS}$ sized to pass into lumen 78 of guide 70. Spacing sleeve 580 also includes a proximal lip 582 of distal end region 581 which abuts against proximal edge 79 of guide 70 when spacing sleeve 580 is inserted into guide 70. The proximal end 583 of spacing sleeve 580 includes a proximal edge 584. During use, the depth of reaming by reamer 575 is affirmatively stopped when distal edge 577 contacts proximal edge 584 of spacing sleeve 580. It will be appreciated that the arrangement of a guide and spacing sleeve can also be used to provide guidance for a tap, implant driver or other instrument used according to the invention.

FIG. 31 is a side view of a cleaning probe 590 according to the invention. As illustrated, cleaning probe 590 includes an operating end 591, a shaft 592 and a distal tip 593. Cleaning probe 590 can be used to remove bone material which collects within the flutes 578 of the cutting end 579 of a reamer such as reamer 575 in FIG. 30. In addition, although not shown, any of the reamers of the invention (e.g., 350, 500 or 575) or taps (e.g., 600, 650) can include a bore through the longitudinal axis of reamer for passage of cleaning probe 590 therethrough. The bony debris can be collected and used to pack into the chamber of an implant 10.

Figure 32B:
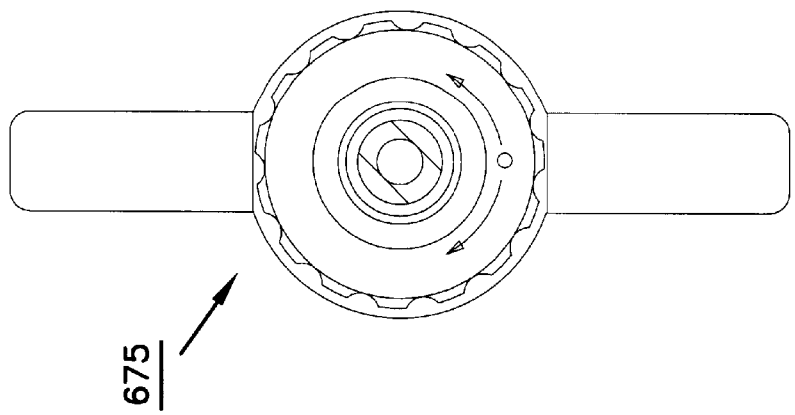
Figure 32A:
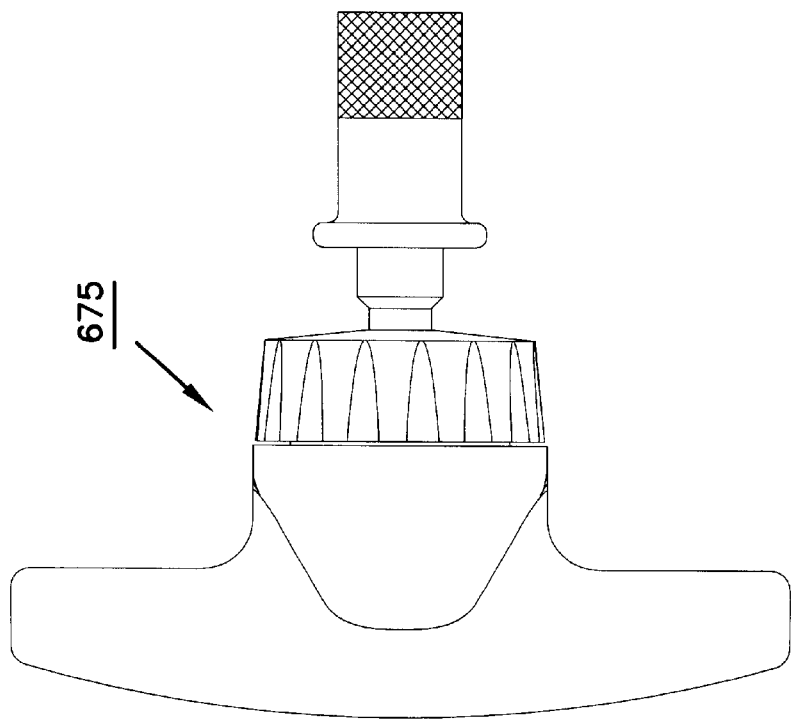
FIG. 32a is a side view of an embodiment of a handle according to the invention.

FIGS. 32a and 32b show a handle 675 suitable for operation of a reamer, tap or driver according to the invention. In this embodiment handle 675 provides a ratchet function using known technology. Non-ratchet handles also be used.

FIGS. 33a–c illustrate an implant driver assembly 700 for inserting an implant (e.g. FIG. 1) in a reamed or reamed and tapped bore. Implant driver 700 includes a proximal end 701 for attaching to a handle (e.g., 675 of FIGS. 32a and 32b) for operating the implant driver 700. Implant driver 700 also has a distal end 702 for mounting of an implant 10 to the implant driver 700. FIG. 33c is a distal end view of implant driver 700 illustrating four protuberances 704a–d which can be inserted into apertures 11a–d at the trailing end 12 of implant 10. The distal end 702 of shaft 705 includes threads 706 for mounting implant driver assembly 700 into threaded bore 13 at the trailing end 12 of implant 10. Once the implant 10 is mounted to implant driver 700, the handle can be rotated so that external threads 14 of implant 10 are threadedly inserted into the implant site bore. Implant driver 700 also can include an adjustable stop 710 which is positioned to affirmatively stop the depth of advancement of an implant 10 into the bore when the distal edge 711 of adjustable stop 710 contacts the proximal edge of a guide or spacing sleeve.

According to the method of the invention, the approximate size of an implant can be determined from x-ray, CT or MRI images of the affected intervertebral disc space. A properly sized implant preferably fits within the perimeter margins of the vertebral bodies. Typically, the appropriate implant size will be based upon the disc height of the affected disc space.

For fusion of a cervical intervertebral space, the patient can be placed in the supine position with support under the cervical spine. The patient can be draped and prepped in the usual manner for an Anterior Cervical Decompression and Fusion (ACDF) surgery. A complete anterior cervical discectomy using conventional methods can be performed. Any bone pieces removed during decompression can be saved for packing into the implant to facilitate fusion.

Based on templating from x-ray, CT or MRI images, the disc space to be fused is distracted using a distraction system such as a Caspar Retractor (Aesculap) or similar retractor. The retractor can be removed or remain in place until the implant has been implanted. The disc space can then be measured by inserting an implant gauge 20 to determine the appropriate disc height. Preferably, the reamer cutting diameter is selected to be approximately 2 to 3 mm greater than the measured disc height.

The paddles of the guide are inserted between the vertebral bodies, and, if an anchoring arrangement is present, the anchoring arrangement is positioned for penetration into the superior and inferior vertebral bodies. To snug the guide into appropriate position, a guide starter is selected having a distal end diameter selected to fit within the lumen of the guide with the shoulder of the guide starter resting on the proximal edge of the ring wall. The end of the guide starter away from the guide can then be tapped with a small mallet to force the paddles into the intervertebral space and wedge the anchoring arrangement into the vertebral bodies. The guide starter can then be removed.

The affirmative stop on the reamer (e.g., lip or distal edge) can be adjusted until the appropriate reaming depth is set. While firmly holding the handle of the guide, the cutting end of the reamer is passed through the lumen of the guide and the reamer advanced until the reamer is affirmatively stopped by the proximal edge of the guide. A lateral x-ray can be taken to inspect the depth of reaming. Typically, in a cervical fusion procedure, ideal reaming is to a depth of about 2 to 3 mm from the posterior margin of the vertebral body. If an insufficient reaming depth has been achieved, the affirmative stop position of the reamer can be adjusted to allow for deeper reaming. To prevent excessive reaming, it is best to make incremental reaming adjustments to achieve the desired depth.

The reamer is then removed from the guide and bone material present in the cutting end can be removed and packed into the implant. The bore can then be tapped. However, in some embodiments of the invention, particularly in methods involving cervical vertebrae, tapping may not be necessary.

After tapping the bore, or if the bore is not tapped, the implant can be mounted to the distal end of an implant driver. The leading end of the implant is inserted into the bore and the implant driver rotated until the implant has been positioned at an appropriate depth. Depending on the size of the components, the guide can be removed prior to inserting the implant or the guide can remain in place and the implant inserted into the bore through the guide.

If two implants are to be inserted, after insertion of the first implant on one side of the intervertebral disc space, the above described procedure is repeated at the second side of the intervertebral disc space. Alternatively, if a dual lumen guide is used, after placement of the guide in the intervertebral disc space, the first implant site can be prepared and, before or after insertion of the first implant into the first implant site, the second implant site prepared. After the implants are inserted, the surgical wound can be closed using known methods.

In a further embodiment, the invention also provides a depth adjustment arrangement, which can advantageously be used to provide for selective control of instrument depth penetration through known elongate hollow guide tubes. In one such embodiment, known taps, reamers and implant guides providing an affirmative stop arrangement at the proximal end of the instrument can be used with the novel hollow guide systems described below.

Figure 36:
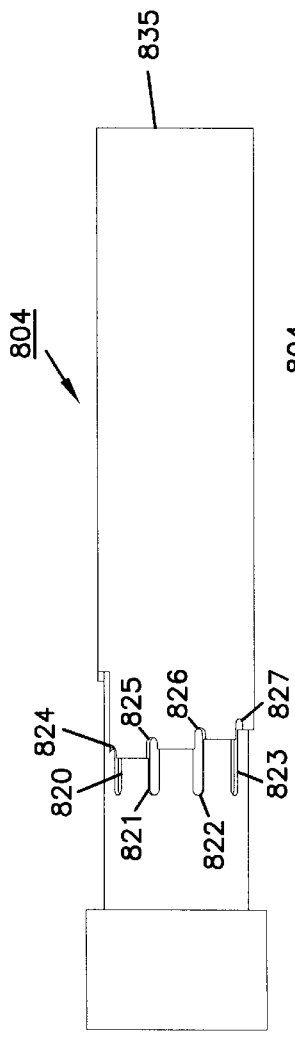
FIG. 36 is a side view of the guide housing of the adjustable guide tube of FIG. 34.
Figure 37:
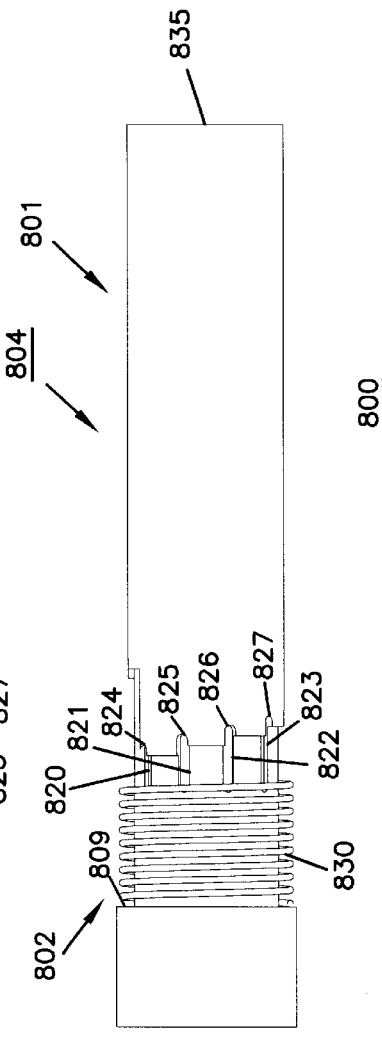
FIG. 37 is a side view of the guide housing of the adjustable guide tube of FIG. 34 with a helical spring in place.
Figure 38:
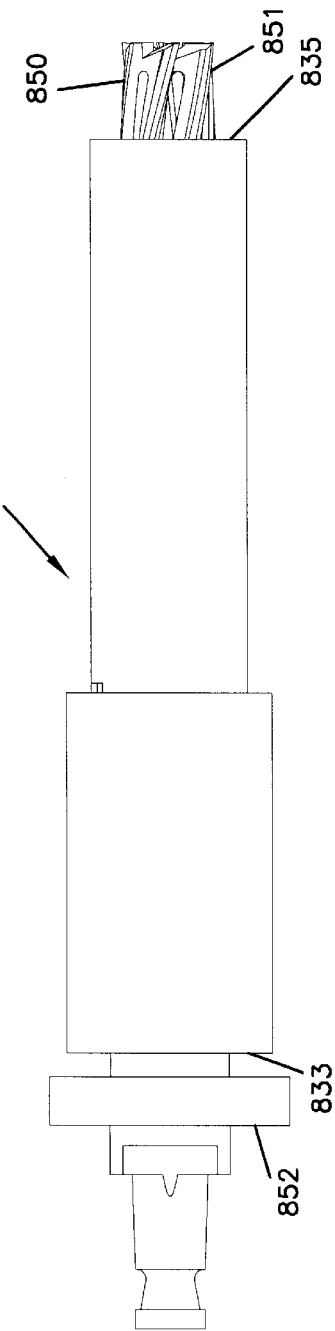
FIG. 38 is a side view of an adjustable guide tube of FIG. 34 with a reaming tool passed therethrough.

FIGS. 34–38 illustrate one embodiment of an adjustable guide tube 800 according to the invention. FIG. 34 is a side view of the adjustable guide tube 800, FIG. 35 is a longitudinal cross section through the adjustable guide tube of FIG. 35. FIG. 36 is a side view of the guide housing of the adjustable guide tube of FIG. 34. FIG. 37 is a side view of the guide housing of FIG. 36 with a helical spring and FIG. 38 is a side view of an adjustable guide tube of FIG. 34 with a reaming tool passed therethrough.

As illustrated, adjustable guide tube 800 has a distal end 801, a proximal end 802 and a lumen 803 passing therethrough. Adjustable guide tube 800 also includes a guide housing 804 and an adjustable sleeve 805. Guide housing 804 includes an inner surface 806 which defines lumen 803 and an outer surface 807 having a proximal cutout 808 which forms a proximal shoulder 809. Adjustable sleeve 805 also has an outer surface 810 and an inner surface 811. Inner surface 811 includes an axially protruding ridge 812 forming a distal shoulder 813.

FIG. 36 illustrates guide housing 804 with adjustable sleeve 805 removed. It will be appreciated that proximal cutout 808 includes a plurality of slots, e.g., 820–823. Each of slots 820–823 include a terminal stop 824–827 which is incrementally positioned a predetermined distance from the distal end 801 of guide housing 804.

Referring again to FIG. 35, the proximal shoulder 809 of guide housing 804 and distal shoulder 813 of adjustable sleeve 805 are biased away from each other by helical spring 830. Adjustable sleeve 805 also includes a pin 831 which protrudes towards inner surface 811 and a proximal rim 832 surrounding opening 833 through which a surgical instrument can pass into the adjustable guide tube. As illustrated in FIG. 26 for adjustable reamer 500, stops 824–827 of adjustable guide tube 800 are preferably oriented in a stair step arrangement spaced around guide housing 804. The stair step arrangement of stops 824–827 permits pin 831 to interdigitate with slots 820–823 and contact stops 824–827 to fix the overall distance between rim 832 of adjustable sleeve 805 and the contact edge 835 of guide housing 804. By sliding adjustment sleeve 805 towards the proximal end 802 of adjustable guide tube 800, pin 831 can be retracted out of a slot (e.g., 820–823) so that when adjustment sleeve 805 is axially rotated, pin 831 can be realigned to pass into an alternate slot.

Once rotated to a selected slot position, adjustable sleeve 805 can slide away from proximal end 802, and pin 831 will advance into the slot to the corresponding stop (e.g., 824–827), by the biasing force of helical spring 830. It will be appreciated that although the foregoing discussion describes four slots 820–823 and four stops 824–827, any number of slots and stops can be used.

According to this embodiment of the invention, once rim 832 of adjustable sleeve 805 is positioned at a selected distance from contact edge 835, adjustable guide tube 800 provides lateral guidance for reamers, taps, implant drivers, etc. which are passed through lumen 803 of adjustable guide tube 800. FIG. 38 illustrates a reamer 850 having a cutting end 851 and a flange 852 which acts as to affirmatively stop penetration of the reamer (or other instrument) when flange 852 contacts rim 832 of adjustment sleeve 805. The distal end 801 of adjustable guide tube 800 can include an anchoring arrangement, paddles, or other features, e.g., longitudinal slots in guide housing 804 for cleaning, present in known hollow guide tube systems.

From the foregoing detailed description and examples, it will be evident that modifications and variations can be made in the devices and methods of the invention without departing from the spirit or scope of the invention. Therefore, it is intended that all modifications and verifications not departing from the spirit of the invention come within the scope of the claims and their equivalents.

What is claimed is:

1. A kit for placement of a spinal implant between opposing vertebral bodies, the kit comprising:
   (a) a first guide for preparing a spinal fusion implant site between said opposing vertebral bodies, said first guide comprising:
   a first ring wall, said first ring wall having a first end, a second end and a first internal ring wall forming a first lumen having a first lumen diameter;
   said first ring wall having a first ring wall length extending from said first end to said second end of said first ring wall;

said guide having an aspect ratio of about 0.5:1 to 3:1;
a first projection extending from said first end of said first ring wall, said projection configured to maintain a desired spacing between the opposing vertebral bodies;

(b) a removable handle adapted to be mounted to said first ring wall; and (c) a guide starter, said guide starter comprising:
a first guide end, said first guide end having a first guide diameter sized for insertion within said first lumen diameter and a second guide diameter which is greater than said first guide diameter.

2. A kit according to claim 1 further comprising a reamer.

3. A kit according to claim 2 wherein the reamer is adjustable.

4. A kit according to claim 1 further comprising, a second guide for preparing a spinal fusion implant site between said opposing vertebral bodies, said second guide comprising:
a second ring wall, said second ring wall having a first end, a second end and a second internal ring wall forming a second lumen having a second lumen diameter, said second lumen diameter different from said first lumen diameter.

5. A kit according to claim 4 wherein said guide starter comprises:
a second guide end longitudinally spaced from said first guide end along a shaft, said second guide end having a third guide diameter sized for insertion within said second lumen diameter and a fourth guide diameter which is greater than said second lumen diameter.

6. A kit according to claim 1 wherein said first ring wall further includes a second internal ring wall forming a second lumen having a second lumen diameter.

7. A kit according to claim 6 wherein said first lumen diameter is equal to said second lumen diameter.

8. A method for preparing a site for implanting a spinal implant into a disc space between adjacent first and second vertebral bodies the method comprising:
distracting said first and second adjacent vertebrae;
engaging a guide with a removable handle, said guide comprising:
(i) a ring wall, said ring wall having a first end, a second end and a first internal ring wall forming a first lumen having a first lumen diameter;
(ii) said ring wall having a first ring wall length extending from said first end to said second end of said ring wall;
(iii) said guide having an aspect ratio of about 0.5:1 to 3:1;
(iv) a first projection extending from said first end of said ring wall, said projection configured to maintain a desired spacing between the opposing vertebral bodies;
(v) a handle receiving structure;
applying said guide over said disc space between distracted first and second adjacent vertebrae; and passing a reamer through said internal ring wall to said disc space and reaming a site for implanting said spinal implant.

9. A method according to claim 8 wherein said guide further comprises a first projection extending from said first end of said ring wall, said projection having a first projection length at least as great as said first ring wall length.

10. A method according to claim 8 further comprising a step of:
removing said guide; and
inserting said implant into said implant site.

11. A method according to claim 10 wherein said implant is inserted into said implant site before said guide is removed.

12. A guide for preparing a spinal fusion implant site between opposing vertebral bodies, said guide comprising:
a wall defining a window, the wall having a length that extends from a first end to a second end, the length of the wall between the first and second ends being measured along a first orientation;
opposing paddles sized for insertion between the opposing vertebral bodies, the paddles projecting outwardly along the first orientation from the first end of the wall;
the window having a window opening dimension measured along a second orientation that extends between the paddles, wherein a ration of the wall length to the window opening dimension is less than about 4:1;
the wall including a first portion and a second portion, the first portion being located between the second portion and the paddles, the first portion defining a first outer dimension measured along the second orientation, the second portion defining a second outer dimension measured along the second orientation, the first outer dimension being smaller than the second outer dimension;
at least one anchoring tooth for penetrating one of the vertebral bodies when the opposing paddles are inserted between the vertebral bodies, the anchoring tooth being located at the first end of the wall and being configured to project outwardly from the first end of the wall along the first orientation; and
a handle removable from the wall for use in inserting the guide between the vertebral bodies.

13. The guide of claim 12, wherein the second portion of the wall and the second portion of the wall abut at a shoulder.

14. The guide of claim 12, wherein the second portion of the wall defines a handle engagement surface that faces away from the paddles.

15. The guide of claim 12, wherein at least one tooth is triangular in shape.

16. The guide of claim 12, wherein the paddles are shorter than the wall length when measure in the first orientation.

* * * * *

UNITED STATES PATENT AND TRADEMARK OFFICE
CERTIFICATE OF CORRECTION

PATENT NO.   : 6,524,318 B1
DATED        : February 25, 2003
INVENTOR(S)  : Longhini et al.

It is certified that error appears in the above-identified patent and that said Letters Patent is hereby corrected as shown below:

Column 14,
Line 23, "704a-dwhich" should read -- 704a-d which --
Line 24, "11a-dat the" should read -- 11a-d at the --

Column 18,
Line 28, "wherein a ration" should read -- wherein a ratio --
Line 48, "claim 12, wherein the second" should read -- claim 12, wherein the first --

Signed and Sealed this

Twenty-third Day of September, 2003

JAMES E. ROGAN
*Director of the United States Patent and Trademark Office*